United States Patent
Moreno et al.

(10) Patent No.: US 10,323,280 B2
(45) Date of Patent: *Jun. 18, 2019

(54) METHODS OF GENOMIC EVALUATION IN LIVESTOCK

(71) Applicant: Inguran, LLC, Navasota, TX (US)

(72) Inventors: Juan F. Moreno, College Station, TX (US); John Dobrinsky, Oregon, WI (US); David Kendall, Beloit, WI (US); Claas Heuer, Heidmoor (DE)

(73) Assignee: Inguran, LLC, Navasota, TX (US)

( * ) Notice: Subject to any disclaimer, the term of this patent is extended or adjusted under 35 U.S.C. 154(b) by 190 days.

This patent is subject to a terminal disclaimer.

(21) Appl. No.: 15/294,179

(22) Filed: Oct. 14, 2016

(65) Prior Publication Data

US 2017/0107572 A1 Apr. 20, 2017

Related U.S. Application Data

(60) Provisional application No. 62/242,828, filed on Oct. 16, 2015, provisional application No. 62/249,018, filed on Oct. 30, 2015.

(51) Int. Cl.
| | |
|---|---|
| *C12N 5/073* | (2010.01) |
| *G16B 20/00* | (2019.01) |
| *A01K 67/027* | (2006.01) |
| *C12N 15/877* | (2010.01) |
| *C12Q 1/6876* | (2018.01) |

(52) U.S. Cl.
CPC ........ *C12Q 1/6876* (2013.01); *A01K 67/0273* (2013.01); *C12N 5/0605* (2013.01); *C12N 15/8771* (2013.01); *G16B 20/00* (2019.02); *A01K 2227/101* (2013.01); *A01K 2267/02* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,496,720 | A | 3/1996 | Susko-Parrish et al. |
| 5,843,705 | A | 12/1998 | DiTullio et al. |
| 6,258,540 | B1 | 7/2001 | Lo et al. |
| 6,781,030 | B1 | 8/2004 | Baguisi et al. |
| 7,592,503 | B2 | 9/2009 | Baguisi et al. |
| 7,612,250 | B2 | 11/2009 | Overstrom et al. |
| 7,893,315 | B2 | 2/2011 | Chung et al. |
| 8,338,098 | B2 | 12/2012 | Khatib et al. |
| 2005/0042595 | A1 † | 2/2005 | Haas |
| 2005/0118712 | A1 | 6/2005 | Tsai et al. |
| 2005/0177883 | A1 | 8/2005 | Rebholtz et al. |
| 2006/0294603 | A1 | 12/2006 | Forsberg et al. |
| 2010/0304978 | A1 | 12/2010 | Deng et al. |
| 2012/0004112 | A1 | 1/2012 | Lund et al. |

FOREIGN PATENT DOCUMENTS

| | | |
|---|---|---|
| WO | 2002/009510 A2 | 2/2002 |
| WO | 2010020252 A1 | 2/2010 |
| WO | 2010033969 A1 | 3/2010 |
| WO | 2014063016 A1 | 4/2014 |

OTHER PUBLICATIONS

Bousquet and Blondin, "Potential Uses of Cloning in Breeding Schemes: Dairy Cattle," Cloning and Stem Cells, vol. 6, No. 2, abstract (2004).
Meuwissen et al., "Prediction of total genetic value using genome-wide dense marker maps," Genetics 157, 1819 1829 (2001).
Van Raden, "Efficient Methods to Compute Genomic Predictions," Dairy Science 91, 4414 4423 (2008).
Prather et al., "Nuclear Transplantation in Early Pig Embryos." Biol. Reprod 41:414-418, 1989.
Campbell et al., "Sheep Cloned by Nuclear Transfer From a Cultured Cell Line." Nature 380:64-66, 1996.
Wilmut et al., "Viable Offspring Derived From Fetal and Adult Mammalian Cells." Nature 385:810-813, 1997.
Szollosi et al., "Remodeling of Mouse Thymocyte Nuclei Depends on the Time of Their Transfer into Activated, Homologous Oocytes." J. Cell Sci. 91:603-613, 1988.
Czolowska et al., "Behavior of Thymocyte Nuclei in Non-Actived and Activated Mouse Oocytes." 1984.
Stice and Robl, "Nuclear Reprogramming in Nuclear Transplant Rabbit Embryos." Biol. Reprod 39:657-664, 1988.
Prather et al., "Nuclear Transplantation in the Pig Embryo: Nuclear Swelling." J. Exp. Zool. 225:355-358, 1990.
Collas and Robl. "Relationship Between Nuclear Remodeling and Development in Nuclear Transplant Rabbit Embryos." Biol. Reprod 45:455-465, 1991.
Smith and Wilmut, "Influence of Nuclear and Cytoplasmic Activity on the Development in Vivo of Sheep Embryos after Nuclear Transplantation." Biol. Reprod. 40:1027 1035, 1989.
Wells et al., "Production of Cloned Lambs from an Established Embryonic Cell Line: A Comparison Between In vivo-and in Vitro-Matured CytoPlasts." Biol. Reprod. 57:385-393, 1997.
Wells et al., "Production of Cloned Calves Following Nuclear Transfer with Cultured Adult Mural Granulosa Cells" Biol. Reprod. 60:996-1005, 1999.
Kato et al., "Eight Calves Cloned from Somatic Cells of a Single Adult" Science 282:2095-2098, 1998.
Prather et al.,"Nuclear Transplantation in the Bovine Embryo: Assessment of Donor Nuclei and Recipient Oocyte" Biol. Reprod. 37:859-866, 1987.
Bondioli et al., "Production of Identical Bovine Offspring by Nuclear Transfer" Theriogenology 33:165-174, 1990.

(Continued)

*Primary Examiner* — John S Brusca
(74) *Attorney, Agent, or Firm* — Ryan Christensen; Hashim Rahman

(57) ABSTRACT

The invention encompasses methods for increasing genetic progress in livestock, and for genetic dissemination, including the use of amniocentesis to obtain fetal amniocytes for use in genomic evaluation and cloning.

24 Claims, 1 Drawing Sheet
Specification includes a Sequence Listing.

(56) References Cited

OTHER PUBLICATIONS

Miller et al., "A Simple Salting Out Procedure for Extracting DNA from Human Nucleated Cells." Nucleic Acids Research. vol. 16 No. 3. 1988.
Biase et al., "Protocol for Extraction of Genomic DNA from Swine Solid Tissues." Genetics and Molecular Biology, No. 25, vol. 3, pp. 313-315 (2002).
Gaillard et al., "The Primary Structure of Bovine Satellite 1.715." vol. 9, No. 22, pp. 6069-6082. 1981, Nucleic Acids Research.
Cibelli, J. B., et al., "Cloned Transgenic Calves Produced from Nonquiescent Fetal Fibroblasts." Science, 280:1256-1258 (1998).
Yong, Z. and L. Yuqiang, "Nuclear-Cytoplasmic Interaction and Development of Goat Embryos Reconstructed by Nuclear Transplantation: Production of Goats by Serially Cloning Embryos." Biol. of Reprod., 58:266-269 (1998).
Presicce and Yang, "Nuclear Dynamics of Parthenogenesis of Bovine Oocytes Matured In Vitro for 20 and 40 Hours and Activated With Combined Ethanol and Cycloheximide Treatment." Mol. Reprod. Dev., 37.61-68 (1994).
Bordignon & Smith, "Telophase Enucleation: An Improved Method to Prepare Recipient Cytoplasts for Use in Bovine Nuclear Transfer." Mol. Reprod. Dev., 49:29-36 (1998).
Bradshaw et al., "UV Irradiation of Chromosomal DNA and Its Effect Upon MPF and Meiosis in Mammalian Oocytes." Molecul. Reprod. Dev., 41:503-512 (1995).
Fulka and Moore, "Noninvasive Chemical Enucleation of Mouse Oocytes." Molecul. Reprod. Dev., 34:427-430 (1993).
Andreau, J. M. and Timasheff, S. N., "Tubulin Bound to Colchicine forms Polymers Different from Microtubules." Proc. Nat. Acad. Sci. 79:6753 (1982).
Obrig, T. G., et al., "The Mechanism by which Cycloheximide and Related Glutarimide Antibiotics Inhibit Peptide Synthesis on Reticulocyte Ribosomes." J. Biol. Chem. 246:174 (1971).
Duskin, D. and Mahoney, W. C., "Relationship of the Structure and Biological Activity of the Natural Homologues of Tunicamycin." J. Biol. Chem. 257:3105 (1982).
Scialli, A. R., et al., "Taxol and Embryonic Development in the Chick." Teratogen, Carcinogen, Mutagen 14:23 (1994).
Nishiyarna, I and Fujii, T., "Laminin-Induced Process Outgrowth from Isolated Fetal Rat C-Cells." Exp. Cell Res. 198:214 (1992).
Small, J. V., et al., "Coumarin—Phalloidin: a New Actin Probe Permitting Triple Immunofluorescence Microscopy of the Cytoskeleton." J. Cell Sci. 89:21 (1988).
Lee, J. C., et al., "Effects of Nocodazole of Structures of Calf Brain Tubulin." Biochem. 19:6209 (1980).
International Search Report and Written Opinion dated May 19, 2017 in related WO application No. PCT/US16/57115.
Gao et al. Multilineage potential research of bovine amniotic fluid mesenchymal stem cells. Int. J Mol Sci Feb. 28, 2014 vol. 15 No. 3 pp. 3698-3710.
Holstein Foundation. Understanding Genetic and the Sire Summaries [online] Jan. 2015 [retrieved Dec. 21, 2016]. Available on the internet: <http://wayne.osu.edu/sites/wayne/files/imce/Program_Pages/ANR/Events/study%20material%20sire%20directories.pdf>.
Da Silva et al. "Production of Bovine Embryos and Calves Cloned by Nuclear Transfer Using Mesenchymal Stem Cells from Amniotic Fluid and Adipose Tissue." Cell Reprogram Apr. 2016 vol. 18 No. 2 pp. 127-136.
European extended Search Report dated Sep. 26, 2017 in related EP application No. 17165604.4.
Ponsart C et al. "Embryo Genotyping : From DNA Amplification to Field Implementation", Proceedings of the 28th Annual Meeting of the European Embryo Transfer Association; Saint Malo, France,; Sep. 7-8, 2012, Sep. 7, 2012 (Sep. 7, 2012), pp. 83-93.
Poothappillai Kasinathan Et Al: "Acceleration if Genetic Gain in Cattle by Reduction of Generation Interval", Scientific Reports, vol. 5, Mar. 2, 2015 (Mar. 2, 2015), p. 8674.
Yudin N S Et Al: "Application of Reproductive Technologies to Improve Dairy Cattle Genomic Selection", Russian Journal of Genetics: Applied Research, , vol. 6, No. 3, May 14, 2016, pp. 321-329.
Cornelissen et al. "Estimating Variance Components and Breeding Values for Number of Oocytes and Number of Embryos in Dairy Cattle Using a Single-Step Genomic Evaluation", Journal of Dairy Science, vol. 100, No. 6, Mar. 30, 2017. pp. 4698-4705.
Cenariu et al. "Evaluation of Bovine Embryo Biopsy Techniques According to Their Ability to Preserve Embryo Viability", Journal of Biomedicine and Biotechnology, vol. 45, No. 5, Jan. 1, 2012,pp. 351-355.
Fisher et al. "Potential for Genomic Selection of Bovine Embryos", Proceedings of the New Zealand Society of Animal Production, vol. 72, Jul. 2, 2012, pp. 156-158.
Campbell et al. "Cell Cycle Co-Ordination in Embryo Cloning by Nuclear Transfer." Reviews of Reproduction (1996) 1, 40-46.
Sinclair et al. "Healthy Ageing of Cloned Sheep." Nature Communications. Jul. 2016.
Melka et al. "Identification of Genomic Differences between Hanwoo and Holstein Breeds Using the Illumina Bovine SNP50 BeadChip." Genomics & Informatics vol. 9(2) 69-73, Jun. 2011.
Harris "Experiences with the Illumina High Density Bovine BeadChip." Interbull Bulletin No. 44. Aug. 2011.
Infinium Assay. Lab Setup and Procedures. 2008, Illumina.
Kamimura, S. et al. "Determining Sex of the Bovine Fetus With Y-Chromosome Specific DNA Amplified by PCR in Fetal Fluid Aspirated by Transvaginal-Transuterine Ultrasound-Guided Amniocentesis." Proceedings, 18th World Buiatrics Congress: 26th Congress of the Italian Association of Buiatrics, Bologna, Italy, Aug. 29 Sep. 2, 1994 vol. 1: 265-268.
Melo et al. "Isolation of transfected fibroblast clones for use in nuclear transfer and transgene detection in cattle embryos" Genetics and Molecular Research 4 (4): 812-821 (2005).
Coleman, Joseph Dewey "Genomic Testing and Method R Variance Components Theory of Dairy Cattle." A Senior Project presented to the Faculty of the Dairy Science Department California Polytechnic University, San Luis Obispo in Partial Fulfillment of the Requirements for the Degree Bachelor of Science by Joseph Dewey Coleman Mar. 2012.
Nana Fan et al. "Piglets Cloned from Induced Pluripotent Stem Cells." Cell Research (2013) 23:162-166. Dec. 18, 2012.
VanRaden et al. "Invited Review: Reliability of Genomic Predictions for North American Holstein Bulls." J. Dairy Sci. 92:16-24. 2009.
Wiggans et al. "The Genomic Evaluation System in the United States: Past, Present, Future." J. Dairy Sci. 94 :3202-3211. 2011.
"Genomic Data Adds Value in Marketing Holstein Sires Globally" ICommunity Newsletter. Aug. 2014.
Form GENO, Description of National Genetic Evaluation Systems. Jun. 18, 2010.
Illumina product listing. Apr. 9, 2013.
Kadarmideen et al. "Genomic Selection of In Vitro Produced and Somatic Cell Nuclear Transfer Embryos for Rapid Genetic Improvement in Cattle Production." Anim. Reprod., v.12, n.3, p. 389-396, Jul./Sep. 2015.
Garrick et al. "Deregressing Estimated Breeding Values and Weighting Information for Genomic Regression Analyses." Genetics Selection Evolution 2009.
Haynes, B. J. et al. "Invited Review: Genomic Selection in Dairy Cattle: Progress and Challenges." J. Dairy Sci. 92:433-443, 2009.
New Zealand Examination Report dated Dec. 20, 2018 issued in related NZ Appl. No. 740961.
Weigel, K. A. "Genomic Selection and its Effects on Dairy Cattle Breeding Programs." Proceedings of 9th WCGALP, 2010.
Weigel et al.; Accuracy of direct genomic values derived from imputed single nucleotide polymorphism genotypes in Jersey cattle; pp. 5423-5435; J. Dairy Sci., vol. 93, No. 11, 2010.†
Schefers, eta l.; GEnomic selection in diary cattleF: Integraton of D testing into breeding programs; pp. 4-9; Jan. 2012, vol. 2, No. 1, Animal Frontiers.†

(56) References Cited

OTHER PUBLICATIONS

Mosca-Boidron, et al.;An Improved Method to Extract DNA from a1 ml of Uncultured Amniotic Fluid from Patients at Less than 16 Weeks' Gestation; pp. 1-10; Apr. 2013, vol. 8, issue 4; PLOS ONE.†

Kasinathan, et al.; Acceleration of genetic gain in cattle by reduction of generation interval; pp. 1-4; Mar. 2, 2015; Scientific Reports.†

Eiras, et al.; Amniotic cell culture during different ages of gestation for karyotype analysis in bovine; pp. 291-295; Braz. J. vet. Res. Anim. Sci. 2000, Sao Paulo, vol. 37, n. 4.†

Taniguchi et al.; Establishment of a method for collective bovine fetal cells from amniotic fluid by transvaginal aspiration; Abstract No. 27;WCAP 2008, Cape Town, South Africa; Book of Abstracts.†

† cited by third party

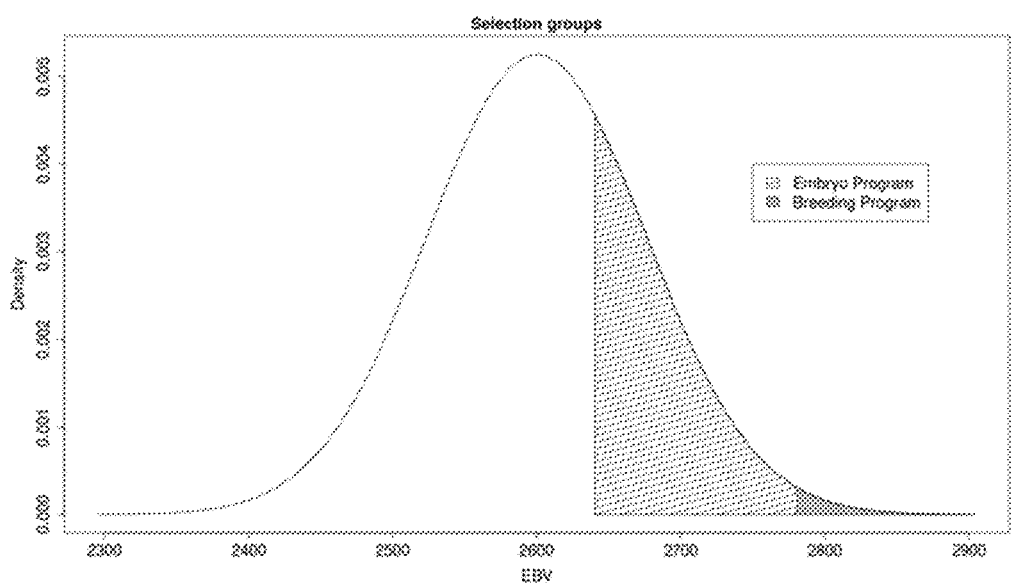

SEQUENCE LISTING

<160> NUMBER OF SEQ ID NOS: 4

<210> SEQ ID NO 1
<211> LENGTH: 21
<212> TYPE: DNA
<213> ORGANISM: Bos taurus

<400> SEQUENCE: 1
gaggctattc ggctatgact g     21

<210> SEQ ID NO 2
<211> LENGTH: 21
<212> TYPE: DNA
<213> ORGANISM: Bos taurus

<400> SEQUENCE: 2
tcgacaagac cggcttccat c     21

<210> SEQ ID NO 3
<211> LENGTH: 30
<212> TYPE: DNA
<213> ORGANISM: Bos taurus

```
<400> SEQUENCE: 3
aggtcgcgag attggtcgct aggtcatgca                              30

<210> SEQ ID NO 4
<211> LENGTH: 29
<212> TYPE: DNA
<213> ORGANISM: Bos taurus

<400> SEQUENCE: 4
aagacctcga gagaccctct tcaacacgt                               29
```

METHODS OF GENOMIC EVALUATION IN LIVESTOCK

REFERENCE TO RELATED APPLICATIONS

This application claims priority from U.S. Provisional Patent Application No. 62/242,828 filed on Oct. 16, 2015, and U.S. Provisional Patent Application No. 62/249,018 filed on Oct. 30, 2015.

REFERENCE TO SEQUENCE LISTING

This application includes a sequence listing which has been submitted electronically in ASCII format and is hereby incorporated by reference in its entirety. Said ASCII copy, created on Dec. 14, 2016, is named ST-59SeqListing.txt and is 4,096 bytes in size.

BACKGROUND OF THE INVENTION

When producing future generations of animals of the highest genetic merit or elite genomic value, a critical selection of potential breeding animals must be made. Only germplasm from the most elite animals can be harvested and used at the genetic nucleus level. Germplasm can include but is not exclusive to gametes such as sperm and oocytes, but also embryos, fetuses, neonates and somatic cells or tissues from living animals.

To that end, genomic testing in the livestock industry has become a valuable tool in evaluating young animals and in increasing genetic progress by increasing the accuracy of selection and decreasing the generation interval. Typically, young animals are genomically tested shortly after birth or as young adults, therefore requiring that significant resources be devoted to supporting the mother during fetal gestation even though the genetic merit of the offspring is unknown.

Embryo transfer is a procedure that follows fertilization (either in vitro or in vivo) and involves the transfer of one or more embryos, from a test tube or the biological mother, to a recipient animal for gestation and birth. Embryo transfer is another tool for increasing genetic progress, since it increases selection intensity by allowing the use of a smaller number of elite females as mothers of many offspring and may also decrease the generation interval in the case where female egg donors are made to ovulate sooner than they normally would be able to give birth. In the livestock industry, the major expense portion of any embryo transfer program is the cost and maintenance of recipient animals into which the embryos are placed for gestation, which may limit its application.

Cloning is yet another tool that can be used to increase genetic progress by increasing the accuracy of selection. See Bousquet and Blondin, "Potential Uses of Cloning in Breeding Schemes: Dairy Cattle," Cloning and Stem Cells, vol. 6, no. 2, abstract (2004). Cloning can also be used to speed up genetic dissemination of genes from animals of exceptionally high genetic merit to the commercial population. Id. The applicability of cloning has to date been limited, however, due to the lag time before a cloned animal can participate in a breeding program. Id. at 193.

Accordingly, there is a need to increase genetic progress and/or genetic dissemination by increasing and improving the use of genomic testing, embryo transfer and cloning in the livestock industry, as well as to reduce the costs and maintenance associated with maintaining recipient animals used in embryo transfer.

SUMMARY OF THE INVENTION

Certain embodiments of the invention encompass a method of determining a genomic estimated breeding value (GEBV) of a non-human mammalian fetus comprising removing amniotic fluid from an amniotic sac containing a viable, non-human mammalian fetus; isolating one or more amniocytes from the amniotic fluid; extracting DNA from the one or more amniocytes; genotyping the DNA to obtain a genotype for the fetus; and determining a GEBV of the fetus based on the genotype. In certain embodiments, the invention further comprises one or more of the following steps: birthing the viable, non-human mammalian fetus; amplifying the DNA; culturing the one or more amniocytes; and creating a clone from the one or more amniocytes using nuclear transfer. In some embodiments of the invention, amniotic fluid is removed or extracted between day 30 and day 90 of gestation of the fetus.

In certain embodiments, the amniocytes for use in the invention are amniotic fluid-derived mesenchymal stem cells. In a specific embodiment, DNA is extracted from ten or fewer such cells. A certain aspect of the invention contemplates that the DNA is genotyped using a BovineSNP50 v1 BeadChip, Bovine SNP v2 BeadChip, Bovine 3K BeadChip, Bovide LD BeadChip, Bovine HD BeadChip, Geneseek® Genomic Profiler™ LD BeadChip or Geneseek® Genomic Profiler™ HD BeadChip. An additional embodiment of the invention further comprises verifying parentage of the fetus based on the genotype.

In other embodiments of the invention, the GEBV is used to determine Genomic Predicted Transmitting Ability (GPTA). In a further embodiments, GEBVs are used in calculating the Genomic Total Performance Index (GTPI®), which is a genomic selection index used in dairy animals. In yet a further embodiment of the invention, it is contemplated that GEBVs and/or GPTAs are estimated or determined for one or more traits, including but not limited to the following: protein; feed efficiency; dairy form; feet and legs composite; somatic cell score; daughter calving ease; fat; udder composite; productive life; fertility index; and daughter stillbirth. In certain embodiments of the invention, feed efficiency is equal to dollar value of milk produced less feed costs for extra milk and less extra maintenance costs. In further embodiments, the fertility index is a function of heifer conception rate, cow conception rate and daughter pregnancy rate.

Other embodiments of the invention encompass a method of determining a GEBV or GPTA of a non-human mammalian fetus comprising extracting DNA from a first fetal amniocyte; genotyping the DNA to obtain a genotype for the fetus; and determining a GEBV of the fetus based on the genotype. In another embodiment, the method further comprises the step of isolating the first fetal amniocyte from amniotic fluid, or the step of cloning the fetus using a second fetal amniocyte. In some embodiments of the invention, the first amniocyte or the second amniocyte comprises an amniotic fluid-derived mesenchymal stem cell.

In certain embodiments, the invention also encompasses a method of increasing the genetic progress in a non-human mammalian line, herd or genetic nucleus, comprising extracting DNA from a first amniocyte derived from a fetus from the line, herd or genetic nucleus; genotyping the DNA to obtain a genotype for the fetus; determining a GEBV or a GPTA of the fetus based on the genotype; selecting the fetus as a parent for the line or herd based on the GEBV or the GPTA; and cloning the fetus to produce a clone. In a further embodiment, the step of cloning the fetus comprises using a second amniocyte derived from the fetus. In yet another embodiment, the first amniocyte or the second amniocyte comprises an amniotic fluid-derived mesenchymal stem cell. In yet another embodiment, the method further comprises the steps of fertilizing an egg from the clone with sperm from a male in the line or herd to produce an embryo; and transferring the embryo into a female recipient for gestation. In certain embodiments, the sperm is sex-sorted sperm of which at least 60% bear an X-chromosome.

Another embodiment of the invention encompasses a method of increasing genetic progress in a population of non-human mammals comprising extracting DNA from one or more amniocytes derived from a fetus from the population; genotyping the DNA to obtain a genotype for the fetus; selecting the fetus as a parent for the population based on the genotype; and cloning the fetus to produce a clone. In a further embodiment, the step of cloning the fetus comprises using an amniocyte derived from the fetus. In another embodiment, the one or more amniocytes comprise amniotic fluid-derived mesenchymal stem cells. In yet a further embodiment, the aforementioned method further comprises the step of determining a GEBV or a GPTA of the fetus based on the genotype. In a specific embodiment of this method, the genotype is an SNP genotype. The aforementioned method may also comprise the additional steps of fertilizing an oocyte from the clone with sperm from a male in the population to produce an embryo; and transferring the embryo into a female recipient for gestation. Finally, in a further embodiment, the sperm is sex-sorted sperm of which at least 60% bear an X-chromosome.

The invention also encompasses a method of genetic dissemination comprising extracting DNA from one or more amniocytes derived from a fetus; genotyping the DNA to obtain a genotype for the fetus; and selecting the fetus as a donor of oocytes for use in IVF based on the genotype. This method may further comprise the steps of collecting one or more oocytes from the donor; and fertilizing the one or more oocytes with sex-sorted sperm to produce one or more female embryos. In a yet a further embodiment, the method may also comprise the step of transferring the one or more female embryos into one or more recipient females. In certain embodiments, the one or more recipient females comprise production animals. This method may also further comprise the steps of producing one or more heifers or cows from the one or more female embryos; and producing milk from the one or more heifers or cows. Finally, in another embodiment, this method may further comprise the step of determining a GEBV or a GPTA of the fetus based on the genotype, and in an even more specific embodiment, the genotype is an SNP genotype.

Embodiments of the invention encompass numerous species of non-human mammals, and the invention should be understood not to be limited to the species of non-human mammals described by the specific examples within this application. Rather the specific examples within this application are intended to be illustrative of the varied and numerous species of non-human mammals to which the methods of the invention may be applied. Embodiments of the invention, for example, encompass animals having commercial value for meat or dairy production such as swine, ovine, bovine, equine, deer, elk, buffalo, or the like (naturally the mammals used for meat or dairy production may vary from culture to culture). They also encompass various domesticated non-human mammalian species such as canines and felines, as well as primates, including but not limited to chimpanzees, and gorillas, as well as whales, dolphins and other marine mammals.

BRIEF DESCRIPTION OF THE DRAWINGS

FIG. 1 shows a distribution of EBVs for a population of selection candidates, including EBVs for animals selected for a breeding program to produce sires and EBVs for animals selected for an embryo production program.

DETAILED DESCRIPTION OF THE INVENTION

The present invention is a novel method encompassing embryo transfer, obtaining an embryonic and/or fetal cell sample from amniotic fluid during gestation, extracting DNA from the cell sample, performing a genomic analysis of the extracted DNA and then cloning the embryo/fetus. In certain embodiments of the invention, the decision to clone an embryo or fetus is based on its genomic analysis, including but not limited to its genomic estimated breeding value with respect to one or more traits.

Certain embodiments of the invention can be used to select against production of animals of inferior or detrimental genetic and/or genomic value, while selecting for the production of the most productive elite genotypes, with the highest call rates, available in a genetic nucleus system. Accordingly, certain embodiments of the invention utilize genomic tools, extensive genetic and genomic evaluation for production, health, fertility and other physiological traits based on analysis of single nucleotide polymorphism (SNP) data from historical reference information, then combine breeding genotypes in a molecular and biotechnology-based breeding program to maximize genetic progress in a line, herd or genetic nucleus. Embryos are created in vivo and in vitro from elite females and bulls to produce offspring with the potential for the highest genetic merit. These embryos are transferred into a highly screened and selected group of recipients maintained on recipient farms. The surrogate females carrying high genetic and/or genomic value pregnancy are monitored during pregnancy, verified for fetal sex and then placed into rotation for amniocentesis-based genetic diagnosis. After organogenesis is complete and fetal growth is underway, fluid and cell aspiration from the fetal amnion is performed. These fluids are collected in a novel aspirate collection system and brought into the laboratory to be placed into cell culture. Aspirate and cells are analyzed by cellular assays and/or genomic approaches, the cells are continued in culture to confluence, passage, cryopreservation or productive use. After genetic and genomic evaluations, genetic information can be used to determine the developmental fate and production direction of any developmentally competent pregnancy. In certain embodiments, selected genetic and genomic based genotypes are placed into a component somatic cloning system to propagate the most elite lines of genotypes. Breeders of non-human mammalian species are focused on increasing the rate of genetic progress in a line, herd or genetic nucleus, as well as on increasing the rate of genetic dissemination of superior genotypes. In furtherance of these goals, tools such as genomic testing, embryo transfer and cloning are being developed and utilized by breeders at various stages of animal production.

Embryo transfer is extensively used in the modern livestock industry. As noted above, the major expense portion of any embryo transfer program is the cost and maintenance of the recipient animals. Typically, however, these costs are offset by the value of the resulting animal, and generally, the higher the genetic merit of the resulting animal, the higher its commercial value. Accordingly, embryo transfer programs place an emphasis on the production of high genetic merit animals.

One aspect of the instant invention allows a breeder to ascertain the genetic merit of a fetus early in gestation. Terminating the pregnancies of low genetic merit fetuses then allows a breeder to either reduce the number of recipient animals needed in their embryo transfer program, or alternatively, to increase the number of high genetic merit fetuses that can be produced using a given number of recipients over a given period of time. In another embodiment, after ascertaining the genetic merit of a fetus, a breeder may decide to maintain the pregnancy but replace the recipient carrying the fetus with a new recipient; and in yet a further embodiment the new recipient is carrying a fetus.

Another aspect of the instant invention allows a breeder to clone high genetic merit fetuses early in gestation and without harming the fetus. Specifically, fetal cells or tissue obtained for ascertaining genetic merit (via amniocentesis, for example) are used to produce clones via somatic cell nuclear transfer. In contrast to the invention, clones in the livestock industry are typically created from somatic cells obtained from young adult animals, and if derived from an in vitro embryo or fetus, the embryo or fetus is generally discarded or severely compromised after such a procedure. Additionally, even without being subjected to biopsy procedures, embryos created by in vitro fertilization (IVF) have a significantly lower survival rate than their conventional, in vivo counterparts. Accordingly, use of the instant invention raises the probability that the costs associated with genomic testing will be recouped since genomic testing is performed after the embryo has established a successful gestation in the recipient.

Embryo Production In Vivo and In Vitro

In certain embodiments of the invention, embryos may be produced in vivo by traditional methods for synchronized supernumerary follicle production, artificial insemination (AI) and scheduled non-surgical transvaginal catheterized intrauterine embryo recovery. In other aspects of the invention, in vitro produced embryos may be produced in the laboratory by non-typical harvest of oocytes, IVF and embryo culture methodologies. In peripubertal heifers, prophase I immature cumulus oocyte complexes (COCs) are recovered from live standing females by using ultrasound guided transvaginal oocyte recovery (TVOR) system, also referred to as ovum pickup (OPU). In prepubertal heifers, ultrasound guided laparoscopic OPU is employed for COC recovery. When immature COCs are brought into the laboratory, they are placed into typical in vitro maturation (IVM) culture system where the most developmentally capable oocytes undergo spontaneous and programmed meiosis. After an overnight culture period, those oocytes that progress through meiosis I (and accordingly shed their second polar body progressing to metaphase of the second meiotic division) and are morphologically normal (including an intact plasma membrane) are used in IVF. Mature oocytes from individual females are placed into traditional IVF drops and mated to specific sires, using highly screened and accurate sperm capacitation treatments and sperm concentration per oocyte fertilized. Zygotes (day 1) are placed into traditional co-culture system and cultured to uterine stages of development by day 7-8 of culture. Embryos are typically transported to a recipient heifer farm where they are non-surgically transferred. Prior to transfer, embryos may be biopsied or sampled for genetic screening and/or genomic evaluation. Within certain specific stages of embryo development, embryos can be dismantled and used in embryo multiplication procedures and/or cryopreserved for later use. Embryos destined for transfer to synchronized surrogate females are transported to the farm in culture and non-surgically transferred by traditional methods. In certain embodiments, the invention contemplates that recipient females are regularly checked by veterinarians and ongoing pregnancies are monitored on a regular and scheduled basis via transrectal real time ultrasonography.

Embryo Transfer

Although not necessarily required, certain embodiments of the invention encompass embryo transfer. Specifically, in some embodiments, fetal cell samples are obtained from amniotic fluid of a recipient animal into which an embryo has been placed via embryo transfer. In other embodiments of the invention, embryo transfer is used to transfer a cloned embryo into a recipient. Any method known in the art may be used to transfer an embryo into a recipient, including any known surgical or non-surgical method. In alternative embodiments, fetal cell samples are obtained from fetuses that are conceived and that gestate entirely in vivo.

The following surgical and non-surgical methods of embryo transfer are provided by way of non-limiting example only.

In cattle, an embryo can be transferred via mid-line abdominal incision, or a flank incision, to a recipient under general anesthesia. Recipients are placed in squeeze chutes that give access to either flank. The corpus luteum is located by rectal palpation and the flank ipsilateral to the corpus luteum is clipped, washed with soap and water, and sterilized with iodine and alcohol. About 60 ml of 2 percent procaine is given along the line of the planned incision. A skin incision is made about 15 cm long, high on the flank, just anterior to the hip. Muscle layers are separated, and the peritoneum is cut. The surgeon inserts a hand and forearm into the incision, locates the ovary, generally about 25 cm posterior to the incision, and visualizes or palpates the corpus luteum. The uterine horn is exteriorized by grasping and stretching with the thumb and forefinger the broad ligament of the uterus, which is located medial to the uterine horn. A puncture wound is made with a blunted needle through the wall of the cranial one-third of the exposed uterine horn. Using about 0.1 ml of medium in a small glass pipette (<1.5 mm outside diameter), the embryo is drawn up from the storage container. The pipette is then inserted into the lumen of the uterus, and the embryo is expelled. The incision is then closed, using two layers of sutures.

Alternatively, a non-surgical method may be used to transfer an embryo in cattle. First, it is necessary to palpate ovaries in order to select the side of ovulation, since pregnancy rates are lowered if embryos are transferred to the uterine horn contralateral to the corpus luteum. Recipients should be rejected if no corpus luteum is present or pathology of the reproductive tract is noted. The next step is to pass the embryo transfer device, e.g., a standard Cassou inseminating gun, through the cervix. The third step of non-surgical transfer is to insert the tip of the instrument into the desired uterine horn ipsilateral to the corpus luteum. The final step of the procedure is to transfer the embryo from a container, such as a straw, into the desired uterine horn using the transfer device.

Collection of Amniotic Fluid

Certain embodiments of the invention encompass methods of collecting amniotic fluid. Once amniotic fluid is collected, a further aspect includes isolating fetal cells from the amniotic fluid and performing genomic analysis on DNA extracted from the fetal cells. Any method known in the art for collection of amniotic fluid may be used in the invention, including but not limited to trans-vaginal/trans-uterine collection using either ultrasound guided or manual puncture techniques. Additionally, amniotic fluid may be collected at any time during gestation in a mother or embryo transfer recipient, including from day 45 through parturition, or between day 1 to day 10, day 20 to day 30, 30 to day 280, day 40 to day 100, day 50 to day 80, day 60 to day 70, day 70 to day 80, day 80 to day 90, day 90 to day 100, day 100 to day 120, day 70 to day 90, day 75 to day 80, day 75 to day 90, day 70 to day 85, or day 120 to day 280, of gestation.

By way of example, the following collection procedure may be used in the invention. One skilled in the art will know that variations on this method exist and that this method should not be construed to limit the functionality or scope of the current invention. This method is illustrative only.

Obtain a bovine mother, or recipient, with a fetus on day 65 to day 250 of gestation. Administer standard caudal epidural anesthesia with 2% lidocaine. Raise the animals approximately 40 cm at the front using a platform in order to place the reproductive tract back towards the pelvis. Clean and disinfect the vulva region and inside of the vaginal vaults several times with iodine. Trans-rectally retract the uterus with the opposite hand and juxtapose the pregnant horn against the vaginal wall. Insert an ultrasound-transducer covered with a sterile sleeve into the vaginal vault with the aid of light lubrication approximately to the level of the cervix. Aspirate the fetal fluid by intra-vaginal placement of a needle (Ø=1.3 mm, 68 cm length) installed within the body of the ultrasound-transducer and connected to a vacuum-tube blood collection assembly. Ultrasound scanner may be equipped with a 5.0 MHz convex type transducer approximately 1.6 cm wide and 58 cm long. Advance the needle through the vaginal and uterine walls by sharply moving the vacuum tube over a distance of about 3 to 4 cm. If the syringe plunger meets resistance, reposition the needle and take another aspirate. Transfer the aspirate was to a sterile 10 ml test tube, placed on ice, and submit for DNA analysis. Confirm successful needle placement by direct observation of ultrasonography and fetal fluid swirling within the vacuum tube. Fetal viability may be assessed between 7 to 10 days after the aspiration procedure. Imaging of either independent fetal movement or heart beat may be taken as proof of viability.

Another collection method in pregnant cattle encompasses the use of ultrasound-guided transvaginal oocyte recovery (TVOR) equipment, specialized fluid recovery tubing, and adapted filter collection system. In this example, in all cattle destined for amniocentesis, pregnancy is confirmed and fetal sex determined by transrectal ultrasonography at specific periods after embryo transfer, implantation and the completion of organogenesis. By day 45-100, or more specifically day 75-80, of the first trimester of gestation, ultrasound-guided transvaginal oocyte recovery equipment is adapted and used to visualize the entire fetus and amniotic vesicle in a uterine horn during aspiration. Prior to collection, the heifers are restrained in stocks and sedated prior to performing amniocentesis. The veterinary staff performing amniocentesis use complete sterile procedures, including powder free nitrile gloved hands and ethanol sterilization of equipment. To ensure that the area is free of contamination before insertion of the transducer, the rectum is emptied of feces, and under epidural anesthesia the vulva and rectal area of the cow are thoroughly cleaned and scrubbed. The disinfection step is completed by rinsing the vulva and rectal area with Betadine solution and the rinsing and spraying the cleaned area with 70% ethanol. The TVOR equipment is cleaned and sterilized with ethanol immediately prior to its introduction into the vagina and is fitted with a sterile stainless steel single-needle guide. The TVOR equipment is advanced into the vagina, positioned to the left or the right of the cervical os and by means of manipulation per rectum, the pregnant uterine horn is positioned against the probe, avoiding interposition of other tissue in the proposed needle path. The exact location of the amniotic sac is determined by the recognition of fetal body parts, the allantoamniotic and allantochorionic membranes and the uterine wall. When a non-echogenic area representing amniotic fluid is seen on the monitor screen, a sterile needle with a stylette is inserted within the needle guide and advanced penetrating through the vaginal wall, uterus and subsequent fetal membranes. As soon as the tip of the needle is seen to have entered the fetal fluid compartment, the stylette is withdrawn from the needle and the needle is placed inside the amnion of the fetus. An initial 5-10 ml of fetal fluid is aspirated into the tubing and flushed out of the tubing system to reduce or eliminate maternal contamination. An amniocentesis filter is attached to the tubing and an additional 30-40 ml of amniotic fluid is aspirated. During the fluid collection, the pregnant uterine horn is held in the same position, and the exact location of the tip of the needle is guaranteed by its visualization on the ultrasound screen. When samples from more than 1 heifer are collected on the same day, the needle-guide is replaced by a sterile one, and the transducer is thoroughly cleaned and disinfected before being used on the next animal. After collection of amniotic fluid is completed in an animal, the collected fluid in the filter system is placed on ice and transported back to the cell culture laboratory.

Isolating Amniocytes from Amniotic Fluid

The term "amniocytes" as used herein, refers to cells obtained from amniotic fluid, as well as to cells cultured from cells obtained from amniotic fluid. Amniocytes, including fetal fibroblasts and amniotic fluid-derived mesenchymal stem cells (AFMSCs), used in the present invention may be obtained from, e.g., amniotic fluid from amniocentesis performed for fetal karyotyping, or amniotic fluid obtained at term. For purposes of the invention, amniocytes may be isolated from the amniotic fluid by any method known in the art, e.g., by centrifugation followed by removal of the supernatant.

Amniocyte Cell Culture

One aspect of the invention encompasses culturing isolated amniocytes. Cultured amniocytes can in turn be used in various applications, including genotyping and for producing clones. By way of example, the following culturing procedure may be used in certain embodiments of the invention. One skilled in the art will know that variations on this method exist and that this method should not be construed to limit the functionality or scope of the current invention. This method is illustrative only.

Amniocytes are centrifuged (200 g, 10 min) at room temperature and the pellet is gently resuspended in Chang medium. Cells are plated into 100 mm gelatinized Petri dishes and left undisturbed. Media is changed every 3-4 days. After 2 weeks in culture, they are trypsinized to disperse cells and allow their growth in a monolayer. Amniocytes are cultured at 37° C. in a humidified 5% $CO_2$ atmosphere. Cells are passaged at a ratio 1:4 every 5 days until they reach 80% confluence. For subsequent passages, the media is aspirated, washed with PBS, detached with 0.05% trypsin for 5 min at 37° C.

Isolation and Culture of Amniotic Fluid-derived Mesenchymal Stem Cells

In certain embodiments of the invention, a two-stage culture method may be used to isolate, culture, and enrich amniotic fluid-derived mesenchymal stem cells (AFMSCs) from amniotic fluid obtained by amniocentesis. Mammalian mesenchymal stem cells are presumptively multipotent cells that have the potential to differentiate into multiple lineages including bone, cartilage, muscle, tendon, ligament fat and a variety of other connective tissues. Morphologically, mesenchymal stem cells in their undifferentiated state are spindle shaped and resemble fibroblasts. Mesenchymal stem cells have been identified mostly in bone marrow, but have also been found in both adult and fetal peripheral blood, fetal liver, fetal spleen, placenta and in term umbilical cord blood. Significantly, mesenchymal stem cells can be found in mammalian amniotic fluid. Under specific culture conditions, mammalian AFMSCs have been induced to differentiate into adipocytes, osteocytes and neuronal cells.

The two-stage culture protocol comprises a first stage of culturing amniocytes, and a second stage of culturing mesenchymal stem cells. The method begins by setting up primary cultures using cytogenetic laboratory amniocytes culture protocol. Non-adhering amniotic fluid cells in the supernatant medium are collected. For culturing mesenchymal stem cells, the non-adhering cells are centrifuged and then plated in a culture flask with an alpha-modified Minimum Essential Medium supplemented with fetal bovine serum. For mesenchymal stem cell growth, the culture is incubated with humidified $CO_2$.

By way of example, the following specific culturing procedure may be used in certain embodiments of the invention. One skilled in the art will know that variations on this method exist and that this method should not be construed to limit the functionality or scope of the current invention. This method is illustrative only.

For culturing amniocytes, set up four primary in situ cultures in 35 mm tissue culture-grade dishes using Chang medium (Irvine Scientific, Santa Ana, Calif.). Collect non-adhering amniotic fluid cells in the supernatant medium on the 5th day after the primary amniocytes culture and keep them until a completion of fetal chromosome analysis.

For culturing mesenchymal stem cells, centrifuge the tube containing the non-adhering cells, then plate them in 5-15 ml of alpha-modified Minimum Essential Medium (α-MEM) supplemented with 10-20% fetal bovine serum (FBS) and 1-20 ng/ml b-FGF in a 25 $cm^2$ culture flask and incubate at 37° C. with 5% humidified $CO_2$ for mesenchymal stem cell growth.

Flow cytometry, RT-PCR, and immunocytochemistry may be used to analyze the phenotypic characteristics of the cultured mesenchymal stem cells. Von Kossa, Oil Red O and TuJ-1 stainings may be used to assess the differentiation potentials of the mesenchymal stem cells.

The following additional culture method is presented by way of example only. The invention contemplates sterile technique, including being gloved with non-powder nitrile gloves to process amniotic fluid. In certain embodiments of the invention, the entire process is performed in a cell culture laminar flow biosafety cabinet and only food grade ethanol is used in washing gloved hands whenever needed or possible.

Fluid and amniocytes are aspirated by pipette into 15 ml conical tubes. The collection filter is rinsed with culture medium to remove any adhered cells and repeated as necessary to remove a maximal amount of amniocytes from the filter. The conical tubes are centrifuged until a cell pellet is formed, supernatant is aspirated, and cells are resuspended in cell culture medium. The cell suspension is thoroughly mixed and pipetted into culture wells and/or dishes. Cell cultures are placed into a cell culture incubator and cultured at 38.7 C in 5% $CO_2$/air for 5 days undisturbed. On day 5 of culture, cell culture dishes are removed from culture and cell culture medium and any floating cells are aspirated and placed into 15 ml centrifuge tube. The remaining cells plated on the original cell culture dishes, primarily fetal fibroblasts and AFMSCs are fed with fresh culture medium and placed back into cell culture incubators and cultured until 80-90% confluent. After reaching confluency, the cells are lifted for passage and/or cryopreservation. The aspirated floating amniocytes can be started in amniocyte-specific cell culture or used in fetal diagnostic testing and/or genomic testing and profiling. Both original plated fetal fibroblast cultures and original floating amniocyte cell cultures can be cultured for indefinite passaging and cryopreservation. Cryopreserved fetal fibroblasts and/or amniocytes can be warmed and passaged or used in cloning procedures.

DNA Extraction and Amplification

Another aspect of the invention encompasses genotyping amniocytes. Specifically, once fetal fibroblasts or mesenchymal stem cells have been isolated from the amniotic fluid, their DNA may be extracted and used for genotyping. In a specific embodiment, the DNA of cultured fetal fibroblasts or mesenchymal stem cells can be used for genotyping. Fetal fibroblast, or mesenchymal stem cell, DNA may first be extracted and then amplified (via PCR) so that there is a sufficient amount of DNA for genotyping. Alternatively, in some embodiments of the invention, DNA may be extracted directly from amniocytes, including fibroblasts and mesenchymal stem cells, found in amniotic fluid. The invention encompasses embodiments in which the amount of DNA extracted is very low, ranging from 1 ng/μl to 10 ng/μl (based on double strand DNA assays). Visualization using 1% agarose gels has shown the extracted DNA in some examples to be large, ≥23000 MW with little fragmented DNA.

For genomic analysis, approximately 1-200 ng of double stranded DNA should be extracted per sample DNA at concentration per sample of 1-50 ng/ul. In certain embodiments of the invention, only 1 ng/μl to 10 ng/μl of DNA are necessary for genomic analysis. In a particular embodiment, less than 15 ng of DNA total is necessary for genomic analysis. In some embodiments of the invention, the DNA is used in genotyping for parental verification and genomic evaluation. The genomic evaluation for production, health, fertility and other physiological traits utilized in certain embodiments of the invention is based on analysis of SNP data from historical reference population data determined by genome-wide association studies (GWAS). This evaluation of fetal cells also allows for rapid generation modeling by allowing pre-selection of fetus as a parent for the next generation of matings. The remaining cells in culture remain in cell culture for passage and eventual harvest and cryopreservation for later diagnostic, cytogenetic and biological productive use such as cloning.

By way of example, the following DNA extraction and amplification procedure may be used in certain embodiments of the invention. One skilled in the art will know that variations on this method exist and that this method should not be construed to limit the functionality or scope of the current invention. This method is illustrative only.

Fibroblast DNA is extracted from the contents of a 25-cm$^2$ culture bottle by the salting-out procedure, with minor modifications (Miller et al., 1988; Biase et al., 2002). Fifty nanograms of genomic DNA is used in 25 μL of PCR mix (1 U Taq polymerase, 100 μM dNTP, 1 mM MgCl$_2$, 5 pmol of each primer) and amplified 36 times using the following conditions: 93° C. for 3 min, 93° C. for 40 s, 58° C. for 40 seconds, 72° C. for 40 seconds, and 72° C. for 5 min. The primers are designed to amplify a 410-bp fragment of the NeoR gene (sense: 5'-GAG-GCT-ATT-CGG-CTA-TGA-CTG-3' (SEQ ID NO: 1) and anti-sense: 5' -TCG-ACA-AGA-CCG-GCT-TCC-ATC-3' (SEQ ID NO: 2)) and a 262-bp fragment of bovine satellite I DNA (Gaillard et al., 1981) (sense: 5'-AGG-TCG-CGA-GAT-TGG-TCG-CTA-GGT-CAT-GCA-3' (SEQ ID NO: 3) and anti-sense: 5'-AAG-ACC-TCG-AGA-GAC-CCT-CTT-CAA-CAC-GT-3' (SEQ ID NO: 4)).

In certain embodiments of the invention, DNA from amniocytes and mesenchymal stem cells can be extracted using the Purelink Genomic Kit Cat # K1820-00 (Invitrogen). In further embodiments, once the DNA is extracted, it can be put through a whole genome amplification protocol using the Illustra Genomiphi V2 DNA amplification kit (GE Lifesciences), which uses the phi29 DNA polymerase to amplify the genome.

In other embodiments of the invention the following DNA extraction procedure is employed.

Cells exposed to culture media often contain fetal calf serum. Due to high levels of DNase commonly found in fetal calf serum and the presence of cations that could catalyze the hydrolytic cleavage of phosphodiester linkage in DNA, an equal volume of a solution containing Tris-EDTA is added to the harvested cells to chelate cations essential for DNase activity. After adding the Tris-EDTA, the cell suspension is then stored in 1.5 ml microcentrifuge tubes at 4° C. until required for DNA extraction.

The 1.5 ml tubes containing cell suspension are spun at ≥10000×g in a microcentrifuge for 45 seconds to pellet cells. The suspension solution is pipetted off carefully so as to not remove pelleted cells. Approximately 50 μl of suspension solution is left in the tube. The tubes are then vortexed for 10 seconds to resuspend the cell pellets. 300 μl of Tissue and Cell Lysis Solution (Epicentre; Madison Wis.) containing 1 μl of Proteinase K (Epicentre; Madison Wis.) are then added to each tube and mixed. The tubes are then incubated at 65° C. for 30 minutes while making sure to vortex at 15 minutes. The samples are then cooled to 37° C. Afterwards 1 μl of 5 mg/μl RNase A (Epicentre; Madison Wis.) is added to each sample and then mixed. The samples are then incubated at 37° C. for 30 minutes. The samples are then placed in a 4° C. cooler for 5 minutes. 175 μl of MPC Protein Precipitation Reagent (Epicentre; Madison Wis.) are then added to each sample, and the samples are then vortexed vigorously for 10-15 seconds. The samples are then centrifuged in order to pellet debris for 8 minutes at ≥10000×g. The supernatant is then transferred to a clean microcentrifuge tube. 600 μl of cold (−20° C.) isopropanol is added to the supernatant. Each tube is then inverted 30-40 times. The DNA is then pelleted by centrifugation for 8 minutes in a microcentrifuge at ≥10000×g. The isopropanol is poured off without dislodging DNA pellet. The pellet is rinsed once with 70% ethanol and then the ethanol is carefully poured off so as not to disturb the DNA pellet. The residual ethanol is then removed with a pipet, and the DNA pellet is allowed to air dry in the microcentrifuge tube. Once dried, resuspend the DNA pellet in 20 μl Tris-EDTA.

Genotyping DNA

In one aspect of the invention, extracted and/or amplified DNA from amniocytes and mesenchymal stem cells may be genotyped using SNP arrays or chips, which are readily available for various species of animals from companies such as Illumina and Affymetrix. For purposes of the invention, the term "genotyping" includes, but is not limited to, obtaining SNP and/or copy number variation (CNV) data from DNA. For purposes of the invention, the term "genotype" includes, but is not limited to, SNP and/or copy number variation (CNV) data obtained from DNA. Low density and high density chips are contemplated for use with the invention, including SNP arrays comprising from 3,000 to 800,000 SNPs. By way of example, a "50K" SNP chip measures approximately 50,000 SNPs and is commonly used in the livestock industry to establish genetic merit or genomic estimated breeding values (GEBVs). In certain embodiments of the invention, any of the following SNP chips may be used: BovineSNP50 v1 BeadChip (Illumina), Bovine SNP v2 BeadChip (Illumina), Bovine 3K BeadChip (Illumina), Bovide LD BeadChip (Illumina), Bovine HD BeadChip (Illumina), Geneseek® Genomic Profiler™ LD BeadChip, or Geneseek® Genomic Profiler™ HD BeadChip.

Determining GEBVs from SNP Data

The basis, and algorithm, for using SNPs in determining GEBVs is found in Meuwissen et al., "Prediction of total genetic value using genome-wide dense marker maps," Genetics 157, 1819 1829 (2001), which is incorporated by reference herein in its entirety. Implementation of genomic data in predictions for desirable traits is found in Van Raden, "Efficient Methods to Compute Genomic Predictions," Dairy Science 91, 4414 4423 (2008), which is incorporated by reference herein in its entirety.

Livestock in the United States are often ranked using selection indexes that incorporate data related to various commercially important traits. With the advent of genomic testing, genomic data is now commonly used to predict these traits. To calculate an animal's score for a genomic selection index, one must first calculate the animal's GEBVs for each trait in the index, which can be accomplished using the teachings in Meuwissen et al. and VanRaden, above. Next, one determines the economic weight for each trait in the index. Finally, to determine the animal's score for the selection index, multiply each trait's GEBV by its economic weight and then sum all of these values together.

A genomic index commonly used in the United States for dairy cattle is the Genomic Total Performance Index (GTPI®), which is comprised of the following traits: protein; feed efficiency; dairy form; feet and legs composite; somatic cell score; daughter calving ease; fat; udder composite; productive life; fertility index; and daughter stillbirth. In certain embodiments, feed efficiency is equal to the dollar value of milk produced less feed costs for extra milk and less extra maintenance costs, and the fertility index is a function of heifer conception rate, cow conception rate and daughter pregnancy rate. In other embodiments of the invention, GEBV is used to determine Genomic Predicted Transmitting Ability (GPTA).

By way of example, in addition to determining a GEBV for a trait, the presence or absence of any of the following diseases and/or traits can be detected using SNP data or genomic data: Demetz syndrome; white heifer disease; Weaver syndrome (haplotype BHW); haplotype HHD; haplotype HH1; lethal brachygnathia trisomy syndrome; haplotype HH0; bovine hereditary cardiomyopathy; bovine dilated cardiomyopathy; neuronal ceroid lipofuscinosis;

bovine chondrodysplastic dwarfism; notched ears/nicked ears; idiopathic epilepsy; bilateral convergent strabismus with exophthalmos; haplotype BHP; haplotype HHP; haplotype JHP; neuropathic hydrocephalus/water head; congenital hypotrichosis and anodontia defect/ectodermal dysplasia; ichthyosis fetalis; lethal trait A46/bovine hereditary zinc deficiency; Marfan Syndrome; double muscling; multiple ocular defects; bovine ocular squamous cell carcinoma; pink tooth; posterior paralysis/hind-limb paralysis; haplotype BHM; bovine spongiform encephalopathy/mad cow disease; mule foot disease (haplotype HEIM); myophosphorylase deficiency; dropsy; black/red coat color (haplotype HBR; haplotype HEIR); BAND3 deficiency; Charolais ataxia; bovine spinal dysmyelination (haplotype BHD); Dun coat color in Dexter cattle; bovine familial convulsions and ataxia; bulldog calf; simmental hereditary thrombopathy; GHRD; renal tubular dysplasia (RTD)/chronic interstitial nephritis; Hereford white face; haplotype HHC; developmental duplications; black kidney; cardiomyopathy/Japanese black cattle; crooked tail syndrome; congenital pseudomyotonia; bovine hereditary arthrogyposis multiplex congentia; belted; Syndrome d'Hypoplasie Généralisée Capréoliforme; fawn calf syndrome; bovine neonatal pancytopenia; rat-tail syndrome; cheilognathoschisis; German White Fleckvieh syndrome; haplotype JH1; paunch calf syndrome; acorn calf disease/congenital joint laxity and dwarfism; haplotype HH2; haplotype HH3; haplotype HH4; Holstein bull-dog dwarfism; haplotype AH1; haplotype HH5; haplotype JH2; and lethal arthrogyposis syndrome.

Cloning

An additional aspect of the invention encompasses cloning embryos and/or fetuses that have been genomically evaluated using the techniques disclosed herein. Cloning is generally understood to be the creation of a living animal/organism that is essentially genetically identical to the unit or individual from which it was produced. In those embodiments of the invention that encompass cloned embryos and/or fetuses, any method by which an animal can be cloned that is known in the art can be utilized. Thus, it is contemplated that cloned embryos and cloned fetuses are produced by any conventional method, for instance including the cloning techniques described herein, as well as those described in international patent application PCT/US01/41561. In one aspect of the invention, a basis for cloning an embryo or a fetus is its genomic merit. In a further aspect, the embryo or fetus's genetic merit is determined by genomic analysis as disclosed herein.

Cloning of embryos by nuclear transfer has been developed in several species. This technique generally involves the transfer of a cell nucleus (obtained from a donor cell) into an enucleated cell, for instance, a metaphase II oocyte. This oocyte has the ability to incorporate the transferred nucleus and support development of a new embryo (Prather et al., Biol. Reprod 41:414-418, 1989; Campbell et al., Nature 380:64-66, 1996; Wilmut et al., Nature 385:810-813, 1997). Morphological indications of this re-programming are the dispersion of nucleoli (Szollosi et al., J. Cell Sci. 91:603-613, 1988) and swelling of the transferred nucleus (Czolowska et al., 1984; Stice and Robl, Biol. Reprod 39:657-664, 1988; Prather et al., J. Exp. Zool. 225:355-358, 1990; Collas and Robl. Biol. Reprod 45:455-465, 1991). The most conclusive evidence that the oocyte cytoplasm has the ability to re-program is the birth of offspring from nuclear transplant embryos in several species, including sheep (Smith and Wilmut, Biol. Reprod. 40:1027 1035, 1989; Campbell et al., Nature 380:64-66, 1996; Wells et al., Biol. Reprod. 57:385-393, 1997), cattle (Wells et al., Biol. Reprod. 60:996-1005, 1999; Kato et al., Science 282:2095-2098, 1998; Prather et al., Biol. Reprod. 37:859-866, 1987; Bondioli et al., Theriogenology 33:165-174, 1990), pigs (Prather et al., Biol. Reprod. 41:414-418, 1989) and rabbits (Stice and Robl, Biol. Reprod. 39:657-664, 1988).

Cloning by nuclear transfer entails removing the nucleus from the recipient oocyte and isolating a nucleus from a donor cell. The donor nucleus is then joined to the recipient oocyte and electrically induced cell fusion is used to introduce the nuclei from the donor embryo cell into a recipient cell. In certain embodiments, the embryo cloning process follows a basic five step procedure as follows: (1) selecting a proper recipient embryo or oocyte for nuclear transfer; (2) enucleating, i.e., removing the nuclear material from the recipient oocyte; (3) introducing the membrane-bounded nucleus of the donor cell to the enucleated recipient oocyte; (4) orienting the donor membrane-bounded nucleus and the recipient oocyte for cell fusion; and (5) fusing the membrane surrounding the donor nucleus to the membrane of the recipient oocyte and activating the recipient oocyte by dielectrophoresis.

In certain embodiments of the invention, the oocyte used as the recipient cell is a cell that develops from an oogonium and, following meiosis, becomes a mature ovum. In certain embodiments relating to bovines, metaphase II stage oocytes, can be matured either in vivo or in vitro. In some embodiments, mature metaphase II oocytes may be collected surgically from either nonsuperovulated or superovulated cows or heifers 35 to 48 hours past the onset of estrus or past an injection of human Chorionic Gonadotropin (hCG) or similar hormone. Alternatively, in other embodiments, immature oocytes may be recovered by aspiration from ovarian follicles obtained from slaughtered cows or heifers and then may be matured in vitro by appropriate hormonal treatment and culturing.

In certain embodiments of the invention, micromanipulation of cells may performed using a cell holding pipette, having an outer diameter of about 120 micrometers and an inner diameter of approximately 25 to 35 micrometers, and a beveled, sharpened enucleation and transfer pipette having an outer diameter of approximately 25 to 35 micrometers. Mature oocytes may be first treated with cytochalasin B at about 7.5 micrograms per milliliter, or an effectively similar microtubal inhibitor at a concentration sufficient to allow the enucleation and transfer pipette to be inserted through the zona pellucida to allow for removal of a portion of the cytoplasm without, at any point, actually rupturing the plasma membrane. The mature oocyte can be held in place by mild suction by the cell holding pipette. The enucleation and transfer pipette can then be inserted through the zona pellucida of the oocyte at the point of either the metaphase II bulge or adjacent to the first polar body, i.e., in a location intended to be adjacent to the metaphase chromosomes. The pipette does not penetrate the plasma membrane. Aspiration applied through the pipette draws a cellular bulge into the pipette which includes, in the case of the metaphase II bulge, the entire bulge and surrounding cytoplasm, or, in the case of the first polar body, the polar body plus the surrounding cytoplasm. This process is intended to draw all the metaphase chromosomes into the pipette. As the pipette is withdrawn, with suction maintained, the plasma membrane is stretched and then seals to itself leaving a competent plasma membrane on the enucleated oocyte.

In some embodiments of the invention, the donor cells may be treated with cytochalasin B, or may not be, depending on the size of the transfer pipette. The transfer pipette carrying the aspirated membrane-bounded nucleus can be inserted through the zona pellucida of the recipient enucleated oocyte, and the membrane-bounded nucleus can then deposited under the zona pellucida with its membrane abutting the plasma membrane of the recipient oocyte.

In some embodiments of the invention, fusion of the membrane-bounded nucleus to the enucleated recipient oocyte and simultaneous activation of the recipient oocyte may be carried out by a single dielectrophoresis step using commercially available electrofusion equipment. Prior to electrofusing the donor embryo nucleus and enucleated recipient oocyte together, it is necessary to orient the cell membranes in the electric field. The term "orientation" as used herein is defined as the placement of the two cells such that the plane of contact of the two membranes, i.e., the plasma membrane of the body carrying the donor nucleus and the plasma membrane of the recipient oocyte, which will become fused together, is perpendicular to the electrical field. It has been found that random orientation results in a marked reduction in the successful fusion rate. If cells are oriented such that the fusion membranes are parallel, or at approximately a 45° angle, to the electrical field, the rate of successful fusion will decrease. The alignment may be done electrically or mechanically. If the size of the two cells is not greatly disproportionate, a small alignment alternating-current voltage (~5 volts per millimeter at 1000 KHz) for a short time (10 seconds) will cause the cells to reorient with their membranes apposed. Repeated pulses may be needed. If the cells vary greatly in size, mechanical manipulation may be required to properly orient the membranes.

In some embodiments of the invention, the insertion of a membrane-bounded nucleus into an enucleated bovine oocyte may be conducted by a dielectrophoretic method of cell fusion, using a DC current and using a non-conductive, i.e., non-ionic, cell fusion medium such as a mannitol solution or Zimmerman cell fusion medium. The fusion phenomenon is the result of cell membrane breakdown and pore formation between properly oriented opposing cells. The pores, or small channels, created between the two cells are thermodynamically unstable because of the high surface curvature of the channels and the associated high tension in the membrane. This instability causes the channels to merge and enlarge until the membranes form a single cell.

The embryonic single-celled clones produced as described herein preferably are cultured, either in vivo or in vitro, to the morula or blastula stage. For example, the clones may be cultured in sheep oviducts or in a suitable culture medium. The embryos then may be transferred into the uteri of cattle, or other suitable animals, at a suitable stage of estrus. The procedures for embryo transfer are commonly known and practiced in the embryo transfer field. A percentage of these embryo transfers will initiate pregnancies in the maternal surrogates. Live calves born of these pregnancies will be genetically identical where the donor cells were from a single embryo or a clone thereof.

In one embodiment of the invention, cloning can be performed in one step using the nucleus of a somatic cell, such as a fetal fibroblast, or a stem cell, such as a mesenchymal stem cell. The somatic cell or stem cell is fused with an enucleated oocyte. After culture, many of the fused couplets (or cybrids) develop into morulae that can be implanted in recipients for gestation.

In a further embodiment, two or more cycles of cloning can be carried out in order to increase the efficiency of production of cloned animals. Two-step cloning, for example, involves a first cloning cycle (e.g., by nuclear transfer) using a donor cell, growing the resultant cybrid in vitro and/or in vivo to produce a clonal fetus, then using a fetal cell from the clonal fetus for a second round of cloning (e.g., also by nuclear transfer). In one example, a fibroblast is fused with an enucleated oocyte and cultured to about the morula stage. The viable morulae resulting from this procedure are transferred to recipients. Most of these first-cycle pregnancies can be allowed to attempt to reach term, for instance for use as an internal experimental control. After the embryo has developed into a fetus (generally for a sufficient amount of time to display differentiation into tissues and organs), at least one and up to several of these first-cycle fetuses are removed surgically to provide tissue for the production of tissue cultures. By way of example, cattle fetuses can generally be used after they have reached a gestational age of at least 30 days; in specific embodiments, cattle fetuses can be sacrificed at about 45 days gestational age. Alternatively, instead of sacrificing the fetus, amniocytes can be removed from the recipient via amniocentesis as described herein. Any fetal tissue or cells can serve to produce cell cultures. In representative embodiments, fetal cell cultures are produced from fetal fibroblasts, gonadal cells, mesenchymal stem cells or cells from the genital ridge. The fetal cell cultures are propagated and samples preserved (e.g., frozen) for future use. In certain embodiments, fetal tissue is used directly for the second round of cloning (without an intervening storage stage, and in some instances without development of an in vitro cell culture).

The fetal cell cultures (e.g., fibroblast cultures) can be used as nuclear donors for the second cloning cycle. In this second cycle (the second "step" of two-step cloning), fetal cultured cells are fused with enucleated oocytes to produce second-generation morulae. These morulae are transferred to recipients and the resulting pregnancies allowed to go to term to produce live progeny. Pregnancies resulting from the transfer of fetal-origin, second-generation cloned-embryos are allowed to mature for the full gestation period and result in the delivery of live calves.

In certain embodiments, both the donor cell and the oocyte must be activated. An activated (e.g., non-quiescent) donor cell is a cell that is in actively dividing (e.g., not in a resting stage of mitosis). In particular, an activated donor cell is one that is engaged in the mitotic cell cycle, such as G1 phase, S phase or G2/M phase. The mitotic cell cycle has the following phases, G1, S, G2 and M. The G2/M phase refers to the transitional phase between the G2 phase and M phase. The commitment event in the cell cycle, called START (or restriction point), takes place during the G1 phase. "START" as used herein refers to late G1 stage of the cell cycle prior to the commitment of a cell proceeding through the cell cycle. The decision as to whether the cell will undergo another cell cycle is made at START. Once the cell has passed through START, it passes through the remainder of the G1 phase (i.e., the pre-DNA synthesis stage). The S phase is the DNA synthesis stage, which is followed by the G2 phase, the stage between synthesis and mitosis. Mitosis takes place during the M phase. If prior to START, the cell does not undergo another cell cycle, the cell becomes arrested. In addition, a cell can be induced to exit the cell cycle and become quiescent or inactive. A "quiescent" or "inactive" cell, is referred to as a cell in G0 phase. A quiescent cell is one that is not in any of the above-mentioned phases of tile cell cycle. Preferably, the invention utilizes a donor cell is a cell in the G1 phase of the mitotic cell cycle.

In certain embodiments of the invention, the donor cells are synchronized. Using donor cells at certain phases of the cell cycle, for example, G1 phase, allows for synchronization of the donor cells. One can synchronize the donor cells by depriving (e.g., reducing) the donor cells of a sufficient amount of nutrients in the media that allows them to divide. Once the donor cells have stopped dividing, then the donor cells are exposed to media (serum) containing a sufficient amount of nutrients to allow them to being dividing (e.g., mitosis). The donor cells begin mitosis substantially at the same time, and are therefore, synchronous. For example, the donor cells are deprived of a sufficient concentration of serum by placing the cells in 0.5% Fetal Bovine Serum (FBS) for about a week. Thereafter, the cells are placed in about 10% FBS and they will begin dividing at about the same time. They will enter the G1 phase about the same time, and are therefore, ready for the cloning process.

Methods of determining which phase of the cell cycle a cell is in are known to those skilled in the art, for example, U.S. Pat. No. 5,843,705 to DiTullio et al., Campbell, K. H. S., et al., Embryo Transfer Newsletter, vol. 14(1):12-16 (1996), Campbell, K. H. S., et al., Nature, 380:64-66 (1996), Cibelli, J. B., et al., Science, 280:1256-1258 (1998), Yong, Z. and L. Yuqiang, Biol. of Reprod., 58:266-269 (1998) and Wilmut, I., et al., Nature, 385:810-813 (1997). For example, as described below, various markers are present at different stages of the cell cycle. Such markers can include cyclines D 1, 2, 3 and proliferating cell nuclear antigen (PCNA) for G1, and BrDu to detect DNA synthetic activity. In addition, cells can be induced to enter the G0 stage by culturing the cells on a serum-deprived medium. Alternatively, cells in G0 stage can be induced to enter into the cell cycle, that is, at G1 stage by serum activation (e.g., exposing the cells to serum after the cells have been deprived of a certain amount of serum).

In certain embodiments, the genome of the donor cell can be the naturally occurring genome, for example, for the production of cloned animals, or the genome can be genetically altered to comprise a transgenic sequence, for example, for the production of transgenic cloned animals.

In some embodiments of the invention, the oocytes used in the present invention are activated oocytes. Activated oocytes are those that are in a dividing stage of meiotic cell division, and include metaphase I, anaphase I, anaphase II, and preferably, telophase II. Oocytes in metaphase II are considered to be in a resting state. The oocytes can be in the resting stage of metaphase II, and then activated, using methods described herein. The stage that the oocyte is in can be identified by visual inspection of the oocyte under a sufficient magnification. Oocytes that are in telophase II are identified, for example, by the presence of a protrusion of the plasma membrane of a second polar body. Methods for identifying the stage of meiotic cell division are known in the art.

Oocytes are generally activated by increasing their exposure to calcium levels, in certain embodiments. Increasing levels of calcium, e.g., by between about 10% and about 60% above the baseline levels, induces activation or meiotic cell division of the oocyte. Baseline levels are those levels of calcium found in an inactive oocyte. Rising levels of calcium, coupled with decreasing levels of phosphorylation further facilitates activation of the oocyte. Several methods exist that allow for activation of the oocyte. In particular, a calcium ionophore (e.g., ionomycin) is an agent that increases the permeability of the oocyte's membrane and allows calcium to enter into the oocyte. As the free calcium concentration in the cell increases during exposure to the ionophore, the oocyte is activated following reduction in MPF (maturation promoting factor) activity. Such methods of activation are described in U.S. Pat. No. 5,496,720. Ethanol has a similar affect. Prior to or following enucleation, an oocyte in metaphase II can be activated with ethanol according to the ethanol activation treatment as described in Presicce and Yang, Mol. Reprod. Dev., 37.61-68 (1994); and Bordignon & Smith, Mol. Reprod. Dev., 49:29-36 (1998). Exposure of calcium to the oocyte also occurs through electrical stimulation. The electrical stimulation allows increasing levels of calcium to enter the oocyte.

As contemplated herein, oocytes can be obtained from a donor animal during that animal's reproductive cycle. For example, oocytes can be aspirated from follicles of ovaries at given times during the reproductive cycle (exogenous hormone-stimulated or non-stimulated). Also at given times following ovulation, a significant percentage of the oocytes, for example, are in telophase. Additionally, oocytes can be obtained and then induced to mature in vitro to arrested metaphase II stage. Arrested metaphase II oocytes, produced in vivo or in vitro can then be induced in vitro to enter telophase. Thus, oocytes in telophase can readily be obtained for use in certain embodiments of the present invention. In particular, oocytes can be collected from a female animal following super ovulations. Oocytes can be recovered surgically by flushing the oocytes from the oviduct of a female donor. Methods of inducing super ovulations in, for example, goats and the collection of the oocytes are described herein.

In certain embodiments of the invention, the cell stage of the activated oocytes correlates to the stage of the cell cycle of the activated donor cell. This correlation between the meiotic stage of the oocyte and the mitotic stage of the donor cell is also referred to herein as "synchronization." For example, an oocyte in telophase fused with the genome of a donor cell in G1 prior to START, provides a synchronization between the oocyte and the donor nuclei in the absence of premature chromatin condensation (PCC) and nuclear envelope breakdown (NEBD).

In some embodiments, invention utilizes an oocyte that is enucleated. As contemplated herein, an enucleated oocyte is one that is devoid of the genome, or one that is "functionally enucleated." A functionally enucleated oocyte contains a genome that is non-functional, e.g., cannot replicate or synthesize DNA. See, for example, Bordignon, V. and L. C. Smith, Molec. Reprod. Dev., 49:29-36 (1998). Preferably, the genome of the oocyte is removed from the oocyte. A genome can be functionally enucleated from the oocyte by irradiation, by x-ray irradiation, by laser irradiation, by physically removing the genome, or by chemical means. Other known methods of enucleation can be used with the present invention to enucleate the oocyte.

The oocyte can also be rendered functionally inactive by, for example, irradiating the endogenous nuclear material in the oocyte. Methods of using irradiation are known to those in the art and are described, for example, in Bradshaw et al., Molecul. Reprod. Dev., 41:503-512 (1995).

To physically remove the genome of an oocyte, one can insert a micropipette or needle into the zona pellicuda of the oocyte to remove nuclear material from the oocyte. In one example, telophase oocytes which have two polar bodies can be enucleated with a micropipette or needle by removing the second polar body in surrounding cytoplasm. Specifically, oocytes in telophase stage of meiosis can be enucleated at any point from the presence of a protrusion in the plasma membrane from the second polar body up to the formation of the second polar body itself. Thus, as used herein, oocytes which demonstrate a protrusion in the plasma membrane, usually with a spindle abutted to it, up to extrusion of a second polar body are considered to be oocytes in telophase.

The oocyte can be rendered functionally inactive also by chemical methods. Methods of chemically inactivating the DNA are known to those of skill in the art. For example, chemical inactivation can be performed using the ctopsoide-cycloheximide method as described in Fulka and Moore, Molecul. Reprod. Dev., 34:427-430 (1993). Certain embodiments of the present invention contemplate enucleating the genome of an oocyte by treating the oocyte with a compound that will induce the oocyte genome (e.g., nuclear chromatin) to segregate into the polar bodies during meiotic maturation thereby leaving the oocyte devoid of a functional genome, and resulting in the formation of a recipient cytoplast for use in nuclear transfer procedures. Examples of agents that will effect such differential segregation include agents that will disrupt 1) cytoskeletal structures including, but not limited to, Taxol® (e.g., paclitaxel), demecolcine, phalloidin, colchicine, nocodozole, and 2) metabolism including, but not limited to, cycloheximide and tunicamycin. In addition, exposure of oocytes to other agents or conditions (e.g. increased or decreased temperature, pH, osmolality) that preferentially induce the skewed segregation of the oocyte genome so as to be extruded from the confines of the oocyte (e.g., in polar bodies) also are included in the preferred method. See, for example, methods to include changes in the cytoskeleton and metabolism of cells, methods that are known to those in the art Andreau, J. M. and Timasheff, S. N., Proc. Nat. Acad. Sci. 79:6753 (1982), Obrig, T. G., et al., J. Biol. Chem. 246:174 (1971), Duskin, D. and Mahoney, W. C., J. Biol. Chem. 257:3105 (1982), Scialli, A. R., et al., Teratogen, Carcinogen, Mutagen 14:23 (1994), Nishiyarna, I and Fujii, T., Exp. Cell Res. 198:214 (1992), Small, J. V., et al., J. Cell Sci. 89:21 (1988), Lee, J. C., et al., Biochem. 19:6209 (1980).

Combination of the activated, enucleated oocyle and the genome from the activated donor cell can occur a variety of ways to form the nuclear transfer embryo. A genome of an activated donor cell can be injected into the activated oocyte by employing a microinjector (i.e., micropipette or needle). The nuclear genome of the activated donor cell, for example, a somatic cell, is extracted using a micropipette or needle. Once extracted, the donor's nuclear genome can then be placed into the activated oocyte by inserting the micropipette, or needle, into the oocyte and releasing the nuclear genome of the donor's cell. McGrath, J. and D. Solter, Science, 226:1317-1319 (1984).

In certain embodiments, the present invention includes combining the genome of an activated donor cell with an activated oocyte by fusion e.g., electrofusion, viral fusion, liposomal fusion, biochemical reagent fusion (e.g., phytoheniaglutinin (PHA) protein), or chemical fusion (e.g., polyethylene glycol (PEG) or ethanol). The nucleus of the donor cell can be deposited within the zona pelliduca which contains the oocyte. The steps of fusing the nucleus with the oocyte can then be performed by applying an electric field which will also result in a second activation of the oocyte. The telophase oocytes used are already activated, hence any activation subsequent to or simultaneous with the introduction of genome from a somatic cell would be considered a second activation event. With respect to electrofusion, chambers, such as the BTX® 200 Embryomanipulation System for carrying out electrofusion are commercially available from for example BTX®, San Diego. The combination of the genome of the activated donor cell with the activated oocyle results in a nuclear transfer embryo.

A nuclear transfer embryo of the present invention is then transferred into a recipient animal female and allowed to develop or gestate into a cloned animal. Conditions suitable for gestation are those conditions that allow for the embryo to develop and mature into a fetus, and eventually into a live animal. For example, the nuclear transfer embryo can be transferred via the fimbria into the oviductal lumen of each recipient animal female. In addition, methods of transferring an embryo to a recipient known to those skilled in the art and are described in Ebert et al., Bio/Technology, 12:699 (1994). The nuclear transfer embryo can be maintained in a culture system until at least first cleavage (2-cell stage) up to the blastocyst stage, preferably the embryos are transferred at the 2-cell or 4-cell stage. Various culture media for embryo development are known to those skilled in the art. For example, the nuclear transfer embryo can be co-cultured with oviductal epithelial cell monolayer derived from the type of animal to be provided by the practitioner.

Another aspect of the present invention includes methods for enucleating an activated oocyte comprising contacting the oocyte with a compound that destabilizes (e.g., disrupts or disassociates) the meiotic spindle apparatus. Disruption of the meiotic spindle apparatus results in disruption of microtubules, chromosomes and centrioles. Such a compound renders the nucleus non-frictional. Examples of such compounds are cochicine, pactiltaxel, nocodazole and preferably, demecolcine.

This aspect of the invention can be used for enucleation in combination with the methods described herein. For example, an activated oocyte can be prepared for nuclear transfer by activating the oocyte (e.g., exposing the oocyte to ethanol or an ionophore), and then subjecting the activated oocyte to a compound that destabilizes the meiotic spindles (e.g., demecolcine). Once the activated oocyte is prepared, then it can be combined with genome from an activated donor cell to result in a nuclear transfer embryo.

The following cloning procedure is provided by way of example only.

Cumulus Oocyte Complexes (COCs). COCs contain immature oocytes that are in prophase of the first meiotic division. They can be obtained from ovaries collected from killed animals at an abattoir, or they can be obtained in vivo by real time ultrasound guided transvaginal oocyte recovery (TVOR), also known as ovum pickup (OPU). OPU-derived COCs can be produced from random or scheduled regular OPUs in conjunction with developing follicular waves on the ovaries. Alternatively, scheduled OPUs can be performed on hormone-stimulated donor females with a regular schedule. All COCs regardless of their source are placed into in vitro maturation (IVM).

Cytoplast Formation. After the completion of in vitro maturation (IVM) of COCs, COCs are processed for enucleation which entails the removal of chromatin (metaphase plate) from mature oocytes. At least 20 h after IVM, COCs are placed into pH stabile TL-Hepes with 1 mg/ml hyaluronidase where they are mixed and gently pipetted to remove their cumulus investments. After oocytes are free of cumulus cells, they are evaluated under stereomicroscopy for their morphology, the presence of a perivitelline space with an extruded first polar body, and the integrity of the cytoplasm is determined. Oocytes with a normal zona pellucida, a distinct perivitelline space with normal polar body formation, and a homogenous cytoplasm are subjectively considered mature oocytes (MOs). All MOs are incubated in a microfilament inhibitor such as cytochalasin-b to effectively depolymerize filamentous actin and relax the plasma membrane of the MO. MOs are incubated with a ultraviolet (UV) light activated DNA-specific fluorochrome Hoechst 33342 to illuminate the metaphase chromosomes under fluorescence microscopy and enable their removal via micromanipulation. Under low incandescent lighting and controlled UV light when needed on an inverted compound microscope, special beveled needles are used to pierce through the zona pellucida and into but not piercing the plasma membrane of the MO, just under the area of the fluorescing metaphase chromosomes. Chromatin is gently aspirated out of the MO with as little cytoplasm as possible as a plasma membrane enclosed karyoplast, effectively leaving the former mature oocyte as a rendered and enucleated cytoplast devoid of all chromatin. These enucleations continue until all MOs have been manipulated into plasma membrane intact cytoplasts.

Preparation of frozen somatic cells. Using aseptic cell culture technique, thaw a cryovial of specific genotype somatic cells in a 37 C water bath for 1 minute, 1-2 days prior to cloning, depending on how the cell line grows in vitro. Using aseptic cell recovery technique in a laminar flow cell culture hood, transfer the warmed contents of the cryovial into a 15 ml centrifuge tube. Add 10 ml of cell culture medium (DMEM; DMEM cell culture medium containing Glutamine, Penicillin-Streptomycin and 20% Fetal Bovine Serum) to the centrifuge tube, gently mixing by swirling as medium drops are added. Centrifuge the tube of cells at 200×rpm for 5-10 minutes. Cells are cultured in a 4-well Nunc tissue culture plate and 100 mm cell culture plate. In the 4-well Nunc plate, add 0.5 ml of DMEM into each well and 2 ml of DMEM into the center well. In the 100 mm cell culture dish, add 12 ml DMEM into the dish. After completion of centrifugation, remove supernatant without disturbing the pellet. The pellet is gently resuspended in 0.5 ml of culture medium. After mixing, 50 µl of cell suspension is added into each of the first two Nunc wells, 25 µl to the third well and 15 µl to the fourth well. The remainder of cells in suspension is placed into the 100 mm dish. All cell cultures are placed into the incubator and cultured at 38.7 C in 5% CO2 and air. On the day of use in cloning, these cells are lifted out of cell culture by protease treatment and free and dissociated cells are placed into an organized culture dish for use in somatic cell nuclear transfer cloning.

Clone Reconstruction. After all MOs are enucleated, cytoplasts are prepared for clone reconstruction. Clone reconstruction is the process by which a somatic cell is placed inside the zona pellucida of a cytoplast, later fused to a cytoplast by electrical pulse fusion, after which the reconstructed clones are processed for activation of reprogramming of the somatic cell and the activation of an maternally driven development and eventual activation of a figurative embryonic genome. Specifically, when holding a cytoplast in a plane where the needle incision for enucleation is in a good focal plane, the enucleation tip picks up a somatic cell and goes through the actual incision from enucleation in the zona pellucida. The somatic cell is then placed next to the plasma membrane. All reconstructions are serially completed.

Oocyte Activation. After clone reconstruction is complete, all reconstructed cytoplasts are placed into an electrofusion chamber containing a conductive sugar alcohol based fusion medium. When the reconstructed cytoplasts are aligned uniformly within the chamber, the cytoplasts are treated with a direct current pulse of 100 volts for 40 µsec. After electrofusion, cytoplasts are washed and cultured allowing the cybrids to complete the fusion process. It generally takes 15-30 minutes for somatic cells to fuse to cytoplasts and chromatin to be incorporated into the cytoplasm. After the fusion process is complete, cybrids are placed into culture medium containing ionomycin, a calcium ionophore molecule used to induce the parthenogenetic activation of a mature oocyte and cause a fertilization-like increase in intracellular calcium. Ionomycin induces oocyte second messenger systems that activate the turn on of the maternal genome and induce cortical granule release outside the plasma membrane. This process is not unlike what happens to the oocyte upon sperm fusion and activation of the maternal genome at the onset of fertilization of the mature oocyte. To enhance the efficiency and completion of parthenogenetic activation after ionomycin treatment, cloned embryos are incubated for about 5 hours in a protein synthesis inhibitor cycloheximide (CHX) which induces the resumption of meiosis processes by inactivation of maturation-promoting factor (MPF) and mitogen-activated protein kinase (MAPK) activity (Tian et al., 2002). Bovine oocytes generally require several hours of CHX treatment after ionomycin-induced activation for proper release from meiotic metaphase arrest and complete activation. It is also during this time that the somatic chromatin is reorganized and reprogrammed for embryo development.

Cloned Embryo Culture. All intact reconstructed cloned embryos are placed into long term culture in bovine specific embryo culture medium supplemented with bovine serum albumin. On day 5, embryos with greater than 8 cells and showing signs of early compaction are supplemented with 10% FBS. On day 6-8, advanced blastocyst stage cloned embryos are packed in transport medium and driven to a recipient farm facility where they are non-surgically transferred into surrogate heifer recipients.

Recipient Heifer Management. Cloned embryos destined for transfer to synchronized surrogate females are transported to the farm in culture tubes and non-surgically transferred by traditional methods into specific recipients. Recipient females are regularly checked by veterinarians and ongoing pregnancies are monitored on a regular and scheduled basis via transrectal real time ultrasonography on a monthly basis through term of pregnancy. All females carrying cloned calves are placed into a gestation and pregnancy maintenance protocol which concludes in scheduled caesarian section and intensive care for the live offspring.

The following additional example of cloning is provided by way of example only.

Oocyte Enucleation. In vivo matured oocytes are collected from donor females. Oocytes with attached cumulus cells or devoid of polar bodies are discarded. Cumulus-free oocytes are divided into two groups: oocytes with only one polar body evident (metaphase II stage) and the activated telophase II protocol (oocytes with one polar body and evidence of an extruding second polar body). Oocytes in telophase II are cultured in M199+10% FBS for 3 to 4 hours. Oocytes that are activated during this period, as evidenced by a first polar body and a partially extruded second polar body, are grouped as culture induced, calcium activated telophase II oocytes (Telophase II-Ca+2) and enucleated. Oocytes that have not activated are incubated for 5 minutes in PBS containing 7% ethanol prior to enucleation. Metaphase II stage oocytes (one polar body) are enucleated with a 25-30 micron glass pipette by aspirating the first polar body and adjacent cytoplasm surrounding the polar body (approximately 30% of the cytoplasm) presumably containing metaphase plate.

Telophase stage oocytes are prepared by two procedures. Oocytes are initially incubated in phosphate buffered saline (PBS, $Ca^{+2}/Mg^{+2}$ free) supplemented with 5% FBS for 15 minutes and Cultured in M 199+10% FBS at 38° C. for approximately three hours until the telophase spindle configuration or the extrusion of the second polar body is reached. All the oocytes that respond to the sequential culture under differential extracellular calcium concentration treatment are separated and grouped as Telophase II-$Ca^{2+}$. The other oocytes that do not respond are further incubated in 7% ethanol in M199+10% FBS for 5-7 minutes (Telophase II-ETOH) and cultured in M199+10% FBS for 2 to 4 hours. Oocytes are then cultured in M199+10%/FBS containing 5 µg/ml of cytochalasin-B for 10-15 minutes at 38° C. Oocytes are enucleated with a 30 micron (OD) glass pipette by aspirating the first polar body and approximately 30% of the adjacent cytoplasm containing the metaphase II or about 10% of the cytoplasm containing the telophase II spindle. After enucleation the oocytes are immediately reconstructed.

Embryo Reconstruction. Somatic cells are harvested on day 7 by trypsinizing (0.025% trypsin/0.5 mM EDTA) (Sigma) for 7 minutes. Single cells are resuspended in equilibrated M199+10% FBS supplemented with 2 mM L-glutamine, penicillin/streptomycin. The donor cell injection is carried out in the same medium as for enucleation. Donor cells are graded into small, medium and large before selection for injection to enucleated cytoplasts. Small single cells (10-15 micron) are selected with a 20-30 micron diameter glass pipette. The pipette is introduced through the same slit of the zona made during enucleation and donor cells are injected between the zone pellucida and the ooplasmic membrane. The reconstructed embryos are incubated in M199 30-60 minutes before fusion and activation.

Fusion and Activation. All reconstructed embryos (ethanol pretreatment or not) are washed in fusion buffer (0.3 M mannitol, 0.05 mM $CaCl_2$, 0.1 mM $MgSO_4$—, 9 mM $K_2HPO_4$, 0.1 mM glutathione, 0.1 mg/ml BSA in distilled water) for 3 minutes before electrofusion. Fusion and activation are carried out at room temperature, in a chamber with two stainless steel electrodes 200 microns apart (BTX® 200 Embryomanipulation System, BTX®-Genetronics, San Diego, Calif.) filled with fusion buffer. Reconstructed embryos are placed with a pipette in groups of 3-4 and manually aligned so the cytoplasmic membrane of the recipient oocytes and donor CFF155-92-6 cells are parallel to the electrodes. Cell fusion and activation are simultaneously induced 32-42 hours post GnRH injection with an initial alignment/holding pulse of 5-10 V AC for 7 seconds, followed by a fusion pulse of 1.4 to 1.8 KV/cm DC for 70 microseconds using an Electrocell Manipulator and Enhancer 400 (BTX®-Genetronics). Embryos are washed in fusion medium for 3 minutes, then they are transferred to M199 containing 5 µg/ml cytochalasin-B (Sigma) and 10% FBS and incubated for 1 hour. Embryos are removed from M199/cytochalasin-B medium and co-cultured in 50 microliter drops of M199 plus 10% FBS with goat oviductal epithelial cells overlaid with paraffin oil. Embryo cultures are maintained in a humidified 39° C. incubator with 5% $CO_2$ for 48 hours before transfer of the embryos to recipient females.

Increasing Genetic Progress in a Genetic Nucleus, Line or Herd Using Clones Generated from Amniocytes Certain aspects of the invention encompass a method of increasing genetic progress in a genetic nucleus, line or herd by using clones generated from amniocytes. Within a genetic nucleus, (or line or herd), once selected, parents that produce the next generation are mated with one another, while avoiding matings between closely related individuals, with the goal of increasing the genetic merit of the next generation. An increase in the genetic merit of the next generation constitutes genetic progress. An increase in genetic merit, in this context, means that for a given trait or set of traits, the individuals in the successive generation will express the desired trait or set of traits more strongly than their parents. With respect to undesirable traits, an increase in genetic merit means the individuals in the successive generation will express the trait or set of traits less strongly than their parents.

Genetic change, including desirable genetic change (i.e., genetic progress per year), ("dG") can be measured as the difference between the average genetic level of all progeny born in one year and all progeny born the following year. The difference is the result of selected parents having higher genetic merit than the average genetic merit of all the selection candidates (the animals available for selection as parents of the next generation). In ideal conditions, this depends upon the heritability ($h^2$) of the trait and the difference between the average performance of selected parents and that of selection candidates. The heritability of a trait ($h^2$) is the proportion of observable differences (phenotypic variance, $\sigma^2_P$) in a trait between individuals within a population that is due to additive genetic (A), as opposed to environmental (E), differences ($h^2 = \sigma^2_A/\sigma^2_P = \sigma^2_A/(\sigma^2_A+\sigma^2_E)$). The difference between the average performance of selected parents and that of all selection candidates (of which the selected parents are a subset) is also known as the selection differential.

The genetic progress per year is the result of genetic superiority of selected males and of selected females. This is expressed in the following equation:

$$dG=\{(R_{IH}*i)_{males}+(R_{IH}*i)_{females}\}*\sigma_H/(L_{males}+L_{females}),$$

Where, R=the accuracy of selection, i=the selection intensity, $\sigma_H$=genetic variation and L=generation interval, for male or female parents.

H=breeding goal that combines genetic merit (g) of the traits (1 to m) that need to be produced weighted by the economic values (v) of the traits ($H=v_1g_1+v_2g_2+ \ldots +v_mg_m$). The economic value is positive if selection is for larger phenotypic values and negative if selection is for smaller phenotypic values.

I=an index that combines all the trait information on the individual and its relatives and is the best estimate of the value of H for the individual.

In a large population, the selection intensity depends upon how many animals are tested and how many are selected—the lower the proportion selected the higher the selection intensity and the larger the genetic progress, all else being equal. Thus, in order to maximize genetic progress, one should rank all tested animals based on the GEBV, for example, and then select the minimum number of top males and females required to maintain the line, breed and/or herd size and to avoid inbreeding problems. This ensures that the average GEBV of selected animals is substantially higher than the average GEBV of all animals tested. In particular through the use of artificial insemination (AI), one needs to select fewer males than females and the selection intensity for males is higher than for females.

The generation interval for males (or females) is the average age of male parents (or female parents) when progeny are born. The annual rate of genetic progress depends on the generation interval and on the superiority of the parent's GEBVs compared to that of the selection candidates. In general, males contribute more to the genetic progress per year than the females.

"Line" as used herein refers to animals having a common origin and similar identifying characteristics. "Genetic nucleus" as used herein refers to one or more populations of male and female animals used to generate selection candidates in a breeding program. "Breeding program" as used herein refers to a system for making genetic progress in a population of animals.

The invention encompasses a method in which GEBVs for a genetic nucleus, line or herd are obtained from DNA extracted from amniocytes rather than from tissue samples obtained from adults. The method generally encompasses the steps of extracting DNA from a first amniocyte derived from a fetus from the genetic nucleus, line or herd; genotyping the DNA to obtain a genotype for the fetus; determining a GEBV of the fetus based on the genotype; selecting the fetus as a parent for the genetic nucleus, line or herd based on the GEBV; and cloning the fetus to produce a clone. As demonstrated in Example 3 below, the use of amniocentesis to obtain amniocytes for genomic evaluation independently results in an increase in selection candidates in the genetic nucleus, line or herd and thereby increases selection intensity and genetic progress. This is because fetuses having low genomic scores can be aborted prior to birth, allowing recipient females to be recycled sooner thereby yielding additional candidates. Furthermore, the use of cloning independently results in a decrease in the number of selected animals and thereby increases selection intensity and genetic progress. This is because multiple copies of a single female parent with a superior genomic score can be used to produce all, or a larger portion, of the required number of replacement heifers for the next generation (as opposed having to select multiple different females in order to produce a sufficient number of replacements).

Once produced, cloned females can be used as parents for the next generation using OPU and IVF, including superovulation. Thereafter, the above steps can be repeated, i.e., embryos resulting from IVF, once transferred into recipients, can be genomically evaluated using their amniocytes and a determination can be made whether they will be parents and thus cloned, or alternatively, aborted.

In certain aspects of this embodiment, it is contemplated that IVF is performed using sex-sorted sperm. The term "sex-sorted sperm" includes a sperm sample that has been processed to skew the ratio of X-bearing chromosome sperm to Y-bearing chromosome sperm. As contemplated herein, "sex sorted sperm" can be created either by separating X- and Y-bearing sperm from one another via, for example, well known techniques using flow cytometry, or alternatively, by killing or otherwise incapacitating sperm bearing the undesired sex chromosome via, for example, laser ablation. In certain embodiments, at least 60%, 70%, 80%, 90%, 98% or 99%, of sperm in a sex-sorted sperm sample, bear an X-chromosome. In other embodiments, at least 60%, 70%, 80%, 90%, 98% or 99%, of sperm in a sex-sorted sperm sample, bear a Y-chromosome.

Another embodiment of the invention that makes use of the high testing capacity achieved using amniocentesis encompasses increasing the number of selected animals and then grouping the selected animals into two different categories: one group of animals is used in a breeding program for generating AI sires, and the other group of animals become oocyte donors for the in vitro production of commercial dairy embryos that are intended for transfer into females on production farms. In a specific embodiment, the breeding program generates selection candidates for both the breeding program and the embryo program. In a further embodiment of the invention, the animals selected for the breeding program comprise animals having higher GEBVs or GPTAs than those animals selected for the embryo program. In a more specific embodiment, the animals selected for the breeding program comprise the top 1% of selection candidates in terms of GEBVs or GPTAs. In a further embodiment, the animals selected for the embryo program comprise the next 29% of selection candidates in terms of GEBVs or GPTAs. These relative percentages can be adjusted upwards or downwards depending on the needs of each program. In a specific embodiment, the animals selected for the breeding program comprise the top 2%, 3%, 4%, 5%, 6%, 7%, 8%, 9% or 10% of selection candidates in terms of GEBVs or GPTAs. Females selected for the embryo program are superovulated and their oocytes collected using any methods known in the art. These oocytes are then used to produce female embryos via IVF using sex-sorted sperm, and then the embryos are transferred into female animals at the commercial dairy farm level to subsequently become production animals. As shown in Example 4, below, this embodiment of the invention is able to produce commercial dairy cows/production animals that exceed the average EBV (or GEBV or GPTA) of the selection candidates. In a specific embodiment of the invention, the selection candidates comprise offspring of parents in a genetic nucleus, line or herd. For purposes of the invention, the term "production animal" comprises an animal that produces, or has produced, milk for commercial sale.

EXAMPLE 1

Cloning Using Cultured Mesenchymal Stem Cells

Step 1. Production of donor embryo via IVF. Prophase I immature COCs were recovered from a peripubertal Holstein heifer using a TVOR system. The immature COCs were brought into the laboratory and placed into an IVM culture system. After an overnight culture period, oocytes that progressed through meiosis I and were morphologically normal, were used in IVF. The mature oocytes were placed into IVF drops and fertilized with a specific concentration of capacitated sperm from a Holstein bull. Zygotes (day 1) were placed into traditional co-culture system and cultured to uterine stages of development by day 7-8 of culture. An embryo was transported to a recipient heifer farm where it was non-surgically transferred into a synchronized recipient female. The pregnancy was monitored on a regular and scheduled basis via transrectal real time ultrasonography.

Step 2. Amniocentesis to obtain amniocytes. On day 76 of the pregnancy, amniocentesis was performed on the recipient female. The female was restrained in stocks and sedated prior to performing the amniocentesis. The recipient's rectum was emptied of feces, and under epidural anesthesia, the vulva and rectal area of the recipient was cleaned and scrubbed. The disinfection step was completed by rinsing the vulva and rectal area with Betadine solution and then rinsing and spraying the cleaned area with 70% ethanol. TVOR equipment was cleaned and sterilized with ethanol immediately prior to its introduction into the vagina and was fitted with a sterile stainless steel single-needle guide. The TVOR equipment was advanced into the vagina, positioned to the left or the right of the cervical os and by means of manipulation per rectum, the pregnant uterine horn was positioned against the probe, avoiding interposition of other tissue in the proposed needle path. The exact location of the amniotic sac was determined by the recognition of fetal body parts, the allantoamniotic and allantochorionic membranes and the uterine wall. When a non-echogenic area representing amniotic fluid was seen on the monitor screen, a sterile needle with a stylette was inserted within the needle guide and advanced penetrating through the vaginal wall, uterus and subsequent fetal membranes. As soon as the tip of the needle was seen to have entered the fetal fluid compartment, the stylette was withdrawn from the needle and the needle was placed inside the amnion of the fetus. An initial 5-10 ml of fetal fluid was aspirated into the tubing and flushed out of the tubing system to reduce or eliminate maternal contamination. An amniocentesis filter was attached to the tubing and an additional 30-40 ml of Amniotic fluid was aspirated. During the fluid collection, the pregnant uterine horn was held in the same position, and the exact location of the tip of the needle was guaranteed by its visualization on the ultrasound screen. The collected fluid in the filter system was placed on ice and transported back to the cell culture laboratory.

Step 3. Processing amniocentesis fluid. Under sterile conditions, the collected fluid and amniocytes were aspirated by pipette into 15 ml conical tubes. The collection filter was rinsed with culture medium to remove any adhered cells and repeated as necessary to remove a maximal amount of amniocytes from the filter. The conical tubes were then centrifuged until a cell pellet was formed. The supernatant was aspirated, and the cells resuspended in cell culture medium. The cell suspension was thoroughly mixed and pipetted into culture dishes. The cell cultures were placed into a cell culture incubator and cultured at 38.7 C in 5% $CO_2$/air for 5 days undisturbed. On day 5 of culture, the cell culture dishes were removed from culture and cell culture medium and any floating cells (mesenchymal stem cells) were aspirated and placed into 15 ml centrifuge tubes. The aspirated floating mesenchymal stem cells were started in a separate cell culture. The remaining cells (fibroblasts) were fed with fresh culture medium and placed back into cell culture incubators and cultured until 80-90% confluent. After reaching confluency (day 20), the fibroblasts were lifted for cryopreservation.

Step 4. DNA extraction from cultured fibroblasts and genomic analysis. The frozen fibroblasts were transported to the facility for DNA extraction and genomic analysis. After thawing, an equal volume of a solution containing Tris-EDTA was added. The cell suspension was then stored in 1.5 ml microcentrifuge tubes at 4° C. until required for DNA extraction.

The 1.5 ml tubes containing cell suspension were spun at ≥10000×g in a microcentrifuge for 45 seconds to pellet the cells. The suspension solution was pipetted off carefully so as to not remove the pelleted cells. Approximately 50 µl of suspension solution was left in each tube. The tubes were then vortexed for 10 seconds to resuspend the cell pellets. 300 µl of Tissue and Cell Lysis Solution (Epicentre; Madison Wis.; Catalog # MTC096H) containing 1 µl of Proteinase K (Epicentre; Madison Wis.; at 50 ug/µl; Catalog #MPRK092) was then added to each tube and mixed. The tubes were incubated at 65° C. for 30 minutes and vortexed at 15 minutes. The samples were cooled to 37° C. Afterwards 1 µl of 5 mg/µl RNase A (Epicentre; Madison Wis.; at 5 mg/ml; Catalog # MPRK092) was added to each sample and then mixed. The samples were then incubated at 37° C. for 30 minutes. The samples were then placed in a 4° C. cooler for 5 minutes. 175 µl of MPC Protein Precipitation Reagent (Epicentre; Madison Wis.; Catalog # MMP095H) was added to each sample, and the samples vortexed vigorously for 10-15 seconds. The samples were centrifuged in order to pellet debris for 8 minutes at ≥10000×g. The supernatant was transferred to a clean microcentrifuge tube. 600 µl of cold (−20° C.) isopropanol was added to the supernatant. Each tube was then inverted 30-40 times. The DNA was pelleted by centrifugation for 8 minutes in a microcentrifuge at ≥10000×g. The isopropanol was poured off without dislodging the DNA pellet. The pellet was rinsed once with 70% ethanol and then the ethanol was carefully poured off so as not to disturb the DNA pellet. The residual ethanol was removed with a pipet, and the DNA pellet was allowed to air dry in the microcentrifuge tube. Once dried, the DNA pellet was resuspended in 20 µl Tris-EDTA. The extraction yielded less than 10 ng/µl double stranded DNA.

The extracted DNA was then analyzed using an Illumina bovine SNP BeadChip. The data generated by the SNP BeadChip was used to confirm parentage of the donor embryo and yielded a GTPI score of 2451.

Step 5. IVM of COCs used in cloning. COCs were obtained from slaughterhouse donors and placed into an IVM culture system. After the completion of IVM, the COCs were processed for enucleation. 20 h after IVM, the COCs were placed into pH stabile TL-Hepes with 1 mg/ml Hyaluronidase, where they were mixed and gently pipetted to remove their cumulus investments. After oocytes were free of cumulus cells, they were evaluated under stereomicroscopy for their morphology, the presence of a perivitelline space with an extruded first polar body, and the integrity of the cytoplasm. Oocytes with a normal zona pellucida, a distinct perivitelline space with normal polar body formation, and a homogenous cytoplasm were considered MOs. MOs were incubated in a microfilament inhibitor and Hoechst 33342. Under low incandescent lighting and controlled UV light on an inverted compound microscope, a beveled needle was used to pierce through the zona pellucida and into the plasma membrane of each MO just under the area of fluorescing metaphase chromosomes. Chromatin was successfully aspirated out of MOs to render enucleated cytoplasts.

Step 6. Preparation of mesenchymal stem cells for cloning. Cultured mesenchymal stem cells from the donor embryo were lifted from culture and placed in 15 ml centrifuge tubes. 10 ml of cell culture medium DMEM was added dropwise to each tube while swirling. The tubes were centrifuged at 200×rpm for 5-10 minutes. Cells were cultured in a 4-well Nunc tissue culture plate and 100 mm cell culture plate. In the 4-well Nunc plate, 0.5 ml of DMEM was added into each well and 2 ml of DMEM was added into the center well. In the 100 mm cell culture dish, 12 ml of DMEM was added into the dish. After completion of centrifugation, the supernatant was removed without disturbing the pellet. The pellet was gently resuspended in 0.5 ml of culture medium. After mixing, 50 µl of cell suspension was added into each of the first two Nunc wells, 25 µl to the third well and 15 µl to the fourth well. The remainder of cells in suspension was placed into the 100 mm dish. All cell cultures were placed into the incubator and cultured at 38.7° C. in 5% $CO_2$ and air. On the day of use in cloning, these cells were lifted out of cell culture by protease treatment and free and dissociated cells were placed into an organized culture dish for use in somatic cell nuclear transfer.

Step 7. Clone reconstruction. Cytoplasts were prepared for clone reconstruction. While holding each cytoplast in a plane where the needle incision for enucleation was in a good focal plane, an enucleation tip was used to pick up a mesenchymal stem cell and then go through the actual incision from enucleation in the zona pellucida. The mesenchymal stem cell was then placed next to the plasma membrane in each cytoplast. Reconstructions were serially completed.

Step 8. Oocyte activation. After clone reconstruction was completed, reconstructed cytoplasts were placed into an electrofusion chamber containing a conductive sugar alcohol based fusion medium. When the reconstructed cytoplasts were aligned uniformly within the chamber, the cytoplasts were treated with a direct current pulse of 100 volts for 40 µsec. After electrofusion, cytoplasts were washed and cultured allowing the cybrids to complete the fusion process. After the fusion process was completed, cybrids were placed into culture medium containing ionomycin. Thereafter, the cloned embryos were incubated for approximately 5 hours in CHX.

Step 9. Cloned embryo culture. All intact reconstructed cloned embryos were placed into long term culture in bovine specific embryo culture medium supplemented with bovine serum albumin. On day 5, embryos with greater than 8 cells and showing signs of early compaction were supplemented with 10% FBS. On day 6-8, advanced blastocyst stage cloned embryos were packed in transport medium and driven to a recipient farm facility where they were non-surgically transferred into surrogate heifer recipients.

Step 10. Recipient Heifer Management and Birth. Cloned embryos were transported to the farm in culture tubes and non-surgically transferred by traditional methods into specific synchronized female recipients. Recipient females were regularly checked by veterinarians and ongoing pregnancies were monitored on a regular and scheduled basis via transrectal real time ultrasonography on a monthly basis through term of pregnancy. A successful pregnancy resulted in the birth of a cloned calf. A genomic analysis from a tissue sample obtained from the calf confirmed that the calf was a clone of the donor embryo.

EXAMPLE 2

Cloning Using Cultured Fibroblasts

The materials and methods employed in Example 1 were used to obtain cloned embryos from a second embryo donor, with the following exceptions: 1) DNA extraction and genomic analysis (as described in Step 4, above) were performed using mesenchymal stem cells obtained on day 5 of culture (as obtained in Step 3, above); and 2) the cloned embryos were created using cryopreserved fibroblasts (as obtained in Step 3, above) instead of mesenchymal stem cells. Additionally, each cryovial of fibroblasts was thawed in a 37° C. water bath for 1 minute, 1-2 days prior to cloning, transferred into a 15 ml centrifuge tube, and then processed in accordance with Step 5, above.

EXAMPLE 3

Cloning of Amniocytes to Increase Genetic Progress

In the following example, the effects of amniocentesis and cloning on genetic progress in a herd, line or genetic nucleus were evaluated using the following parameters and assumptions.
Parameters
   $\sigma_P$=Phenotypic standard deviation
   $h^2$=Heritability
   $\sigma_A = \sqrt{h2} * \sigma_P$ (Additive genetic/genomic standard deviation)
   p=Proportion of selected animals
   r=Accuracy of selection
   z=Quantil
   i=z/p (Intensity of selection)
   $\Delta G = i * \sqrt{h2} * \sigma_P * r$ Assumptions
additive genomic standard deviation
sA=76
Capacity for recipients
N=6000
number of selected individuals
Nsel=150
cloning—this gives the number of clones per female
Nclones=10
gestation length in days
GL=285
Gestation day at Amniocentesis
AD=74
per spot in the barn: how many days of the year is an animal not pregnant?
Days to pregnancy for recipient
DP=32
Days from taking sample to genomic test results (GTPI)
gsO=21
Accuracy genomic test results
r=0.8
Scenarios Genetic progress of the herd, line or genetic nucleus under four scenarios was determined. Genomic evaluation (GTPI) (which results in an increase in the accuracy of selection), is performed in all four scenarios. However, in scenarios 1 and 3, genomic evaluation is conducted using post-birth tissue samples, while in scenarios 2 and 4, genomic evaluation is conducted using amniocytes obtained from amniocentesis. Additionally, in scenarios 1 and 2, no cloning was performed, while in scenarios 3 and 4 cloning was performed. A summary of the four scenarios is as follows.
1. No amniocentesis; no cloning.
2. Amniocentesis; no cloning
3. No amniocentesis; cloning using post-birth tissue sample.
4. Amniocentesis; cloning using amniocytes obtained from amniocentesis.
Calculation of Genetic Progress Per Generation for the Scenarios
function that computes deltaG given the parameters above
deltaG=function(N, Nsel, r, sA) {
  p=Nsel/N
  i=dnorm(qnorm(1−p))/p
  G=i*sA*r
  return(list(G=G, N=N))
}
Glist<-list( )
GClist<-list( )
Glist[[1]]=deltaG(N=N*(365/(GL+DP+gsO)),
  Nsel=Nsel,
  r=r,
  sA=sA)
Glist[[2]]=deltaG(N=N*(365/(AD+DP+gsO)),
  Nsel=Nsel,
  r=r,
  sA=sA)
and with clones
GClist[[1]]=deltaG(N=N*(365/(GL+DP+gsO)),
  Nsel=Nsel/Nclones,
  r=r,
  sA=sA)
GClist[[2]]=deltaG(N=N*(365/(AD+DP+gsO)),
  Nsel=Nsel/Nclones,
  r=r,
  sA=sA)

TABLE 1

| Scenario | Amnio | Cloning | Tested.Animals | delta.G |
|---|---|---|---|---|
| 1 | No | No | 6479 | 179.87 |
| 2 | Yes | No | 17244 | 206.12 |
| 3 | No | Yes | 6479 | 237.66 |
| 4 | Yes | Yes | 17244 | 258.82 |

Results:

The use of amniocentesis to obtain amniocytes for genomic evaluation independently results in an increase in selection candidates and thereby increases selection intensity. This is because fetuses having low genomic scores can be aborted prior to birth, allowing recipient females to be recycled sooner thereby yielding additional candidates. Furthermore, the use of cloning independently results in a decrease in the number of selected animals and thereby increases selection intensity. This is because multiple copies of a single female with a superior genomic score can be used to produce all, or a larger portion, of the required number of replacement heifers for the next generation (as opposed having to select multiple different females in order to produce a sufficient number of replacements). An increase in selection intensity results in an increase in genetic progress, all else being equal.

The use of amniocentesis and cloning together (scenario 4) resulted in the largest increase in genetic progress. See Table 1. The use of cloning alone (scenario 3) was superior to use of amniocentesis alone (scenario 2). The lowest genetic progress was obtained when using neither amniocentesis nor cloning (scenario 1).

EXAMPLE 4

Use Of IvF and Embryo Transfer to Increase Genetic Merit of Production Animals

The high number of individuals that can be tested through the methods described in Example 3, above, increases selection intensity when assuming the number of selected animals per generation to be constant. Another approach of making use of that high testing capacity is to increase the number of selected animals, but group them into two different categories: one group is used in a breeding program for generating AI sires (breeding program=BP). The other group of animals become oocyte donors for the in vitro production of commercial dairy embryos that are intended for transfer into females on commercial/production farms (embryo program=EP).

Assumed Parameters

Number of animals tested through using amniocentesis: 17,244

Average EBV of selection candidates: 2,600

Additive genetic standard deviation (GA): 76

Number of selected animals for breeding program: 150

Number of selected animals for embryo program: 5,000

Outcome

FIG. 1 shows the range over the distribution of breeding values across all selection candidates. The animals for the breeding program constitute the top 1% of selection candidates in terms of EBV, while those for the embryo program make up the next 29% of selection candidates in terms of EBV. This leads to two truncation points of the distribution. The first one defines the lower bound for the EP animals (2,640.15) and the second, the upper EP and lower BP bound (2,780.74). The resulting average EBVs in the two selection groups are 2,684.76 and 2,806.12 for the EP and BP group, respectively. The use of amniocentesis in conjunction with an embryo production program for commercial dairy farms is therefore able to deliver commercial dairy cows that exceed the average EBV of the selection candidates (given the assumed parameters and general concept of the program). Any selected EP donor is assumed to deliver 200 offspring through an intensive IVF program. The 5,000 EP animals in this example will therefore be able to generate 1,000,000 commercial dairy cows.

Although the foregoing invention has been described in some detail, one of ordinary skill in the art will understand that certain changes and modifications may be practiced within the scope of the claims.

What we claim is:

1. A method of determining a genomic estimated breeding value (GEBV) or a genomic predicted transmitting ability (GPTA) of a non-human mammalian fetus comprising:
   extracting DNA from one or more fetal amniocytes;
   genotyping the DNA to obtain a genotype for the fetus; and
   determining a GEBV or a GPTA of the fetus based on the genotype.

2. The method of claim 1, further comprising the step of isolating the one or more fetal amniocytes from amniotic fluid.

3. The method of claim 1, further comprising the step of cloning the fetus using a fetal amniocyte.

4. The method of claim 1, wherein the one or more fetal amniocytes comprise amniotic fluid-derived mesenchymal stem cells.

5. The method of claim 1, wherein the genotype is an SNP genotype.

6. The method of claim 5, wherein the DNA is genotyped using a SNP chip or array.

7. The method of claim 1, further comprising the step of calculating a selection index using the GEBV or the GPTA.

8. The method of claim 1, further comprising the step of calculating a selection index using the GEBV or the GPTA.

9. The method of claim 1, further comprising the step of verifying parentage of the fetus using the genotype.

10. The method of claim 1, wherein the non-human mammalian fetus is a bovid.

11. A method of increasing genetic progress in a population of non-human mammals comprising:
    extracting DNA from one or more amniocytes derived from a fetus from the population;
    genotyping the DNA to obtain a genotype for the fetus;
    selecting the fetus as a parent for the population based on the genotype; and
    cloning the fetus to produce a clone.

12. The method of claim 11, wherein the step of cloning the fetus comprises using an amniocyte derived from the fetus.

13. The method of claim 11, wherein the one or more amniocytes comprise amniotic fluid-derived mesenchymal stem cells.

14. The method of claim 11, further comprising the step of determining a GEBV or a GPTA of the fetus based on the genotype.

15. The method of claim 14, wherein the genotype is an SNP genotype.

16. The method of claim 11, further comprising the steps of
    fertilizing an oocyte from the clone with sperm from a male in the population to produce an embryo; and
    transferring the embryo into a female recipient for gestation.

17. The method of claim 11, wherein the sperm is sex-sorted sperm of which at least 60% bear an X-chromosome.

18. A method of genetic dissemination comprising:
    extracting DNA from one or more amniocytes derived from a fetus;
    genotyping the DNA to obtain a genotype for the fetus; and
    selecting the fetus as a donor of oocytes for use in IVF based on the genotype.

19. The method of claim 18, further comprising the steps of
    collecting one or more oocytes from the donor; and
    fertilizing the one or more oocytes with sex-sorted sperm to produce one or more female embryos.

20. The method of claim 19, further comprising the step of
    transferring the one or more female embryos into one or more recipient females.

21. The method of claim 20, wherein the one or more recipient females comprise production animals.

22. The method of claim 20, further comprising the steps of
    producing one or more heifers or cows from the one or more female embryos; and
    producing milk from the one or more heifers or cows.

23. The method of claim 18, further comprising the step of determining a GEBV or a GPTA of the fetus based on the genotype.

24. The method of claim 23, wherein the genotype is an SNP genotype.

* * * * *